(12) United States Patent
Rhoda

(10) Patent No.: US 8,231,675 B2
(45) Date of Patent: Jul. 31, 2012

(54) INTERVERTEBRAL IMPLANT

(75) Inventor: William S. Rhoda, Drexel Hill, PA (US)

(73) Assignee: Synthes USA, LLC, West Chester, PA (US)

( * ) Notice: Subject to any disclaimer, the term of this patent is extended or adjusted under 35 U.S.C. 154(b) by 1237 days.

(21) Appl. No.: 11/672,593

(22) Filed: Feb. 8, 2007

(65) Prior Publication Data

US 2008/0161922 A1 Jul. 3, 2008

Related U.S. Application Data

(63) Continuation of application No. 10/322,609, filed on Dec. 19, 2002, now Pat. No. 7,192,447.

(51) Int. Cl.
*A61F 2/44* (2006.01)
(52) U.S. Cl. .................................... 623/17.11
(58) Field of Classification Search ............... 623/17.11, 623/17.15, 17.16; 606/246
See application file for complete search history.

(56) References Cited

U.S. PATENT DOCUMENTS

| | | |
|---|---|---|
| 3,867,728 A | 2/1975 | Stubstad et al. |
| 4,309,777 A | 1/1982 | Patil |
| 4,349,921 A | 9/1982 | Kuntz |
| 4,743,256 A | 5/1988 | Brantigan |
| 4,759,766 A | 7/1988 | Buettner-Janz et al. |
| 4,772,287 A | 9/1988 | Ray et al. |
| 4,820,305 A | 4/1989 | Harms et al. |
| 4,834,757 A | 5/1989 | Brantigan |
| 4,878,915 A | 11/1989 | Brantigan |
| 4,904,261 A | 2/1990 | Dove et al. |
| 4,917,704 A | 4/1990 | Frey et al. |
| 4,961,740 A | 10/1990 | Ray et al. |
| 5,026,373 A | 6/1991 | Ray et al. |
| 5,055,104 A | 10/1991 | Ray |
| 5,071,437 A | 12/1991 | Steffee |
| 5,123,926 A | 6/1992 | Pisharodi |
| 5,147,404 A | 9/1992 | Downey |
| 5,192,327 A | 3/1993 | Brantigan |
| 5,306,309 A | 4/1994 | Wagner et al. |
| 5,425,772 A | 6/1995 | Brantigan |
| 5,443,514 A | 8/1995 | Steffee |
| 5,458,638 A | 10/1995 | Kuslich et al. |

(Continued)

FOREIGN PATENT DOCUMENTS

EP 0 307 241 3/1998

(Continued)

OTHER PUBLICATIONS

Information disclosure statements and Notice of Cited References originally submitted in the parent application.

*Primary Examiner* — Eduardo C Robert
*Assistant Examiner* — David Comstock
(74) *Attorney, Agent, or Firm* — Stradley Ronon Stevens & Young, LLP

(57) ABSTRACT

A vertebral implant for fusing adjacent vertebrae or for replacing vertebral bodies is disclosed. The implant is a biocompatible metal, resorbable, or radiolucent implant conforming substantially in size and shape with an end plate of a vertebra. The implant preferably has a wedge-shaped profile to restore disc height and the natural curvature of the spine. The top and bottom surfaces of the implant have areas with a plurality of teeth to resist expulsion and provide initial stability and areas devoid of any protrusions to receive implantation instrumentation. The implant also has a stackability feature. The implant provides initial stability needed for fusion without stress shielding.

32 Claims, 17 Drawing Sheets

U.S. PATENT DOCUMENTS

| | | |
|---|---|---|
| 5,458,643 A | 10/1995 | Oka et al. |
| 5,489,308 A | 2/1996 | Kuslich et al. |
| 5,514,180 A | 5/1996 | Heggeness et al. |
| 5,522,899 A | 6/1996 | Michelson |
| 5,534,029 A | 7/1996 | Shima |
| 5,556,431 A | 9/1996 | Buttner-Janz |
| 5,571,190 A | 11/1996 | Ulrich et al. |
| 5,571,192 A | 11/1996 | Schonhoffer |
| 5,609,635 A | 3/1997 | Michelson |
| 5,609,636 A | 3/1997 | Kohrs et al. |
| 5,645,596 A | 7/1997 | Kim et al. |
| 5,645,598 A | 7/1997 | Brosnahan, III |
| 5,658,335 A | 8/1997 | Allen |
| 5,658,337 A | 8/1997 | Kohrs et al. |
| 5,665,122 A | 9/1997 | Kambin |
| 5,669,909 A | 9/1997 | Zdeblick et al. |
| 5,674,295 A | 10/1997 | Ray et al. |
| 5,683,394 A | 11/1997 | Rinner |
| 5,683,463 A | 11/1997 | Godefroy et al. |
| 5,702,449 A | 12/1997 | McKay |
| 5,702,453 A | 12/1997 | Rabbe et al. |
| 5,716,415 A | 2/1998 | Steffee |
| 5,755,797 A | 5/1998 | Baumgartner |
| 5,766,252 A | 6/1998 | Henry et al. |
| 5,776,199 A | 7/1998 | Michelson |
| 5,782,832 A | 7/1998 | Larsen et al. |
| 5,782,919 A | 7/1998 | Zdeblick et al. |
| 5,824,094 A | 10/1998 | Serhan et al. |
| 5,860,973 A | 1/1999 | Michelson |
| 5,861,041 A | 1/1999 | Tienboon |
| 5,865,845 A | 2/1999 | Thalgott |
| 5,865,846 A | 2/1999 | Bryan et al. |
| 5,865,847 A | 2/1999 | Kohrs et al. |
| 5,865,848 A | 2/1999 | Baker |
| 5,876,457 A | 3/1999 | Picha et al. |
| 5,885,287 A | 3/1999 | Bagby |
| 5,888,222 A | 3/1999 | Coates et al. |
| 5,888,224 A | 3/1999 | Beckers et al. |
| 5,888,227 A | 3/1999 | Cottle |
| 5,888,228 A | 3/1999 | Knothe et al. |
| 5,897,593 A | 4/1999 | Kohrs et al. |
| 5,904,719 A | 5/1999 | Errico et al. |
| 5,961,554 A | 10/1999 | Janson et al. |
| 5,984,922 A | 11/1999 | McKay |
| 5,984,967 A | 11/1999 | Zdeblick et al. |
| 5,989,289 A | 11/1999 | Coates et al. |
| 6,019,793 A | 2/2000 | Perren et al. |
| 6,059,790 A | 5/2000 | Sand et al. |
| 6,059,829 A | 5/2000 | Schlapfer et al. |
| 6,080,158 A | 6/2000 | Lin |
| 6,086,613 A | 7/2000 | Camino et al. |
| 6,096,080 A | 8/2000 | Nicholson et al. |
| 6,096,081 A | 8/2000 | Grivas et al. |
| 6,106,557 A | 8/2000 | Robioneck et al. |
| 6,113,638 A | 9/2000 | Williams et al. |
| 6,123,731 A | 9/2000 | Boyce et al. |
| 6,126,688 A | 10/2000 | McDonnell |
| 6,136,031 A | 10/2000 | Middleton |
| 6,143,032 A | 11/2000 | Schafer et al. |
| 6,143,033 A | 11/2000 | Paul et al. |
| 6,146,420 A | 11/2000 | McKay |
| 6,149,686 A | 11/2000 | Kuslich et al. |
| 6,159,211 A | 12/2000 | Boriani et al. |
| 6,176,882 B1 | 1/2001 | Biedermann et al. |
| 6,200,347 B1 | 3/2001 | Anderson et al. |
| 6,228,118 B1 | 5/2001 | Gordon |
| 6,241,771 B1 | 6/2001 | Gresser et al. |
| 6,245,108 B1 | 6/2001 | Biscup |
| 6,258,125 B1 | 7/2001 | Paul et al. |
| 6,296,647 B1 | 10/2001 | Robioneck et al. |
| 6,296,664 B1 | 10/2001 | Middleton |
| 6,296,665 B1 | 10/2001 | Strnad et al. |
| 6,315,797 B1 | 11/2001 | Middleton |
| RE37,479 E | 12/2001 | Kuslich |
| 6,342,074 B1 | 1/2002 | Simpson |
| 6,344,057 B1 | 2/2002 | Rabbe et al. |
| 6,346,123 B1 | 2/2002 | McKay |
| 6,348,071 B1 | 2/2002 | Steffee et al. |
| 6,350,283 B1 | 2/2002 | Michelson |
| 6,458,159 B1 | 10/2002 | Thalgott |
| 6,482,233 B1 | 11/2002 | Aebi et al. |
| 6,503,279 B1 | 1/2003 | Webb et al. |
| 6,558,424 B2 | 5/2003 | Thalgott |
| 6,656,224 B2 | 12/2003 | Middleton |
| 6,699,288 B2 | 3/2004 | Moret |
| 6,719,794 B2 | 4/2004 | Gerber et al. |
| 6,733,535 B2 | 5/2004 | Michelson |
| 6,758,862 B2 | 7/2004 | Berry et al. |
| 2001/0008980 A1 | 7/2001 | Gresser et al. |
| 2001/0016773 A1 | 8/2001 | Serhan et al. |
| 2001/0016774 A1 | 8/2001 | Bresina et al. |
| 2001/0016777 A1 | 8/2001 | Biscup |
| 2001/0039453 A1 | 11/2001 | Gresser et al. |
| 2001/0043940 A1 | 11/2001 | Boyce et al. |
| 2001/0047208 A1 | 11/2001 | Michelson |
| 2001/0051829 A1 | 12/2001 | Middleton |
| 2001/0056302 A1 | 12/2001 | Boyer, II et al. |
| 2002/0013624 A1 | 1/2002 | Michelson |
| 2002/0016592 A1 | 2/2002 | Branch et al. |
| 2002/0016595 A1 | 2/2002 | Michelson |
| 2002/0022888 A1 | 2/2002 | Serhan et al. |
| 2002/0026243 A1 | 2/2002 | Lin |
| 2002/0026244 A1 | 2/2002 | Trieu |
| 2002/0156528 A1 | 10/2002 | Gau |
| 2002/0169508 A1 | 11/2002 | Songer et al. |
| 2003/0060886 A1 | 3/2003 | Van Hoeck et al. |
| 2003/0208274 A1 | 11/2003 | Davis |

FOREIGN PATENT DOCUMENTS

| | | |
|---|---|---|
| EP | 0 834 295 | 4/1998 |
| EP | 0 974 319 A2 | 1/2000 |
| EP | 1 157 675 | 5/2001 |
| FR | 2 724 312 | 3/1996 |
| FR | 2 727 003 | 5/1996 |
| FR | 2 727 004 | 5/1996 |
| FR | 2 727 005 | 5/1996 |
| FR | 2 736 538 | 1/1997 |
| FR | 2 747 034 A1 | 10/1997 |
| JP | 9 122160 | 5/1997 |
| JP | 2001 187075 | 7/2001 |
| WO | WO 89/09035 | 10/1989 |
| WO | WO 96/22747 | 7/1996 |
| WO | WO 97/15248 | 3/1999 |
| WO | WO 99/09914 | 3/1999 |
| WO | WO 99/66867 | 12/1999 |
| WO | WO 00/13618 | 3/2000 |
| WO | WO 00/23014 | 4/2000 |
| WO | WO 00/74608 | 12/2000 |
| WO | WO 01/03615 | 1/2001 |
| WO | WO 01/08611 | 2/2001 |
| WO | WO 01/15637 | 3/2001 |
| WO | WO 01/68005 | 9/2001 |
| WO | WO 0170144 | 9/2001 |
| WO | WO 01/85069 | 11/2001 |
| WO | WO 02/03895 | 1/2002 |

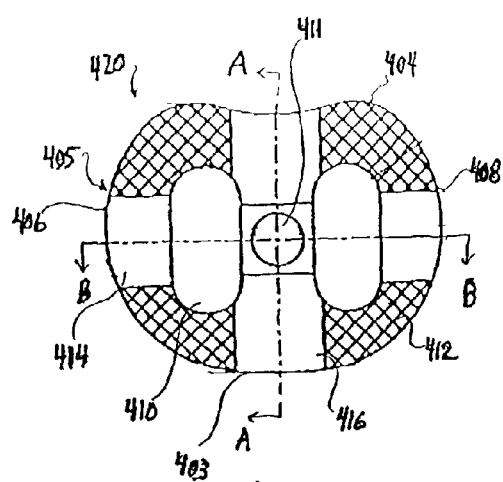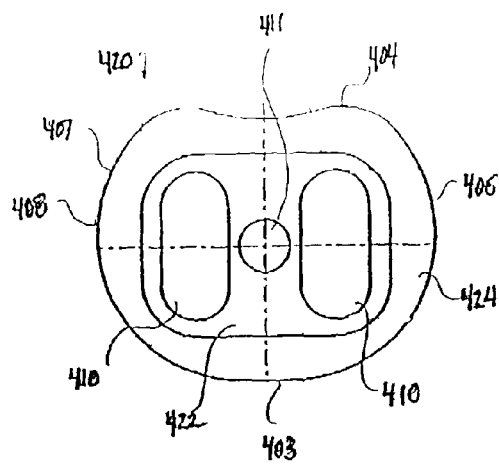
Fig. 22　　　Fig. 23
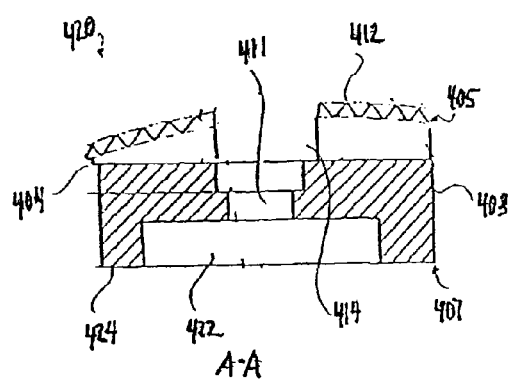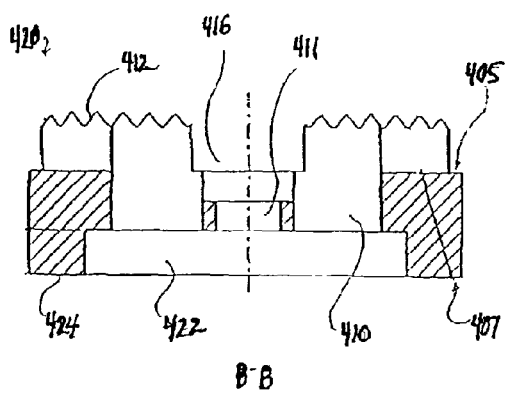
Fig. 24　　　Fig. 25
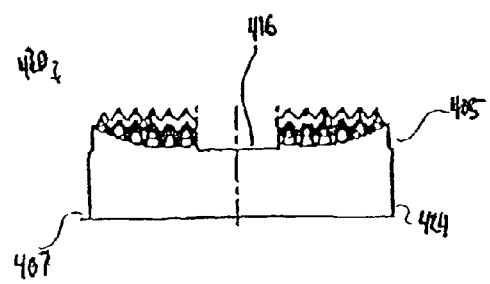
Fig. 26

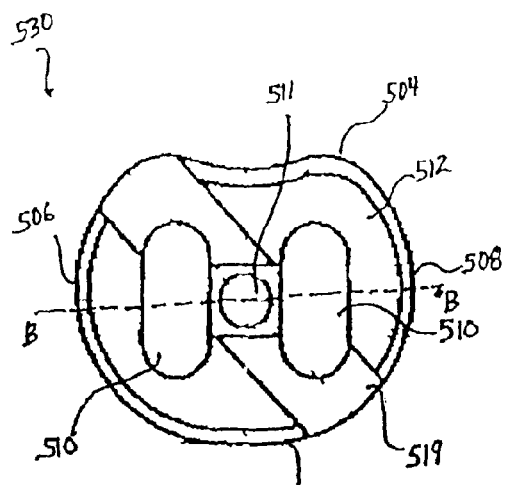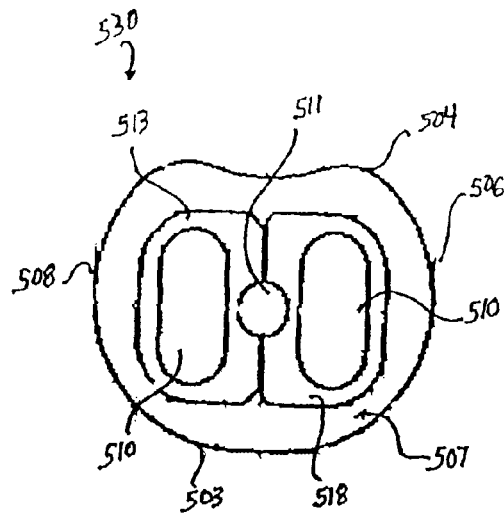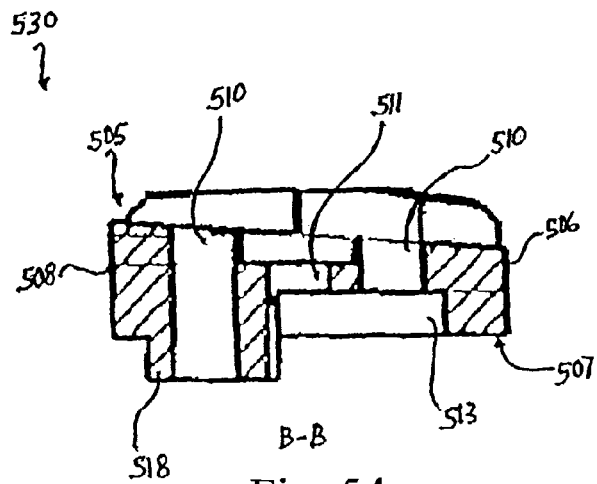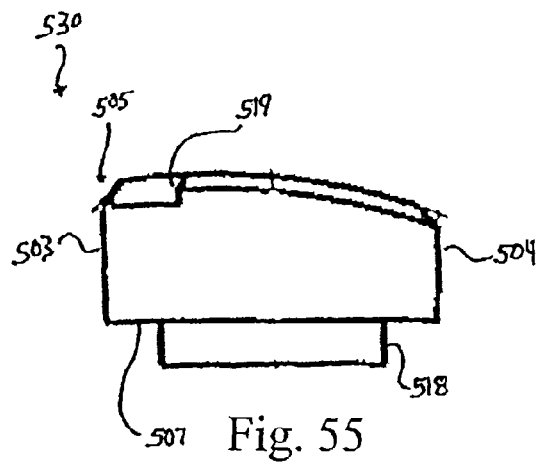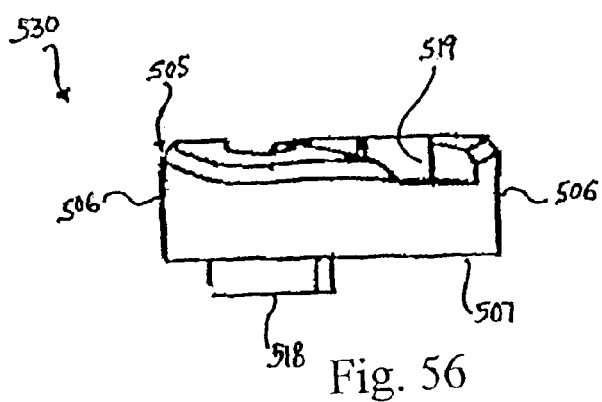

INTERVERTEBRAL IMPLANT

CROSS-REFERENCE TO RELATED APPLICATIONS

This application is a continuation of U.S. application Ser. No. 10/322,609, filed Dec. 19, 2002 now U.S. Pat. No. 7,192,447, the entirety of which is incorporated by reference herein.

FIELD OF THE INVENTION

This invention relates to an artificial biocompatible vertebral device and, more particularly, to an intervertebral spinal implant for use in the treatment of back pain.

BACKGROUND OF THE INVENTION

A number of medical conditions such as compression of spinal cord nerve roots, degenerative disc disease, tumor, and trauma can cause severe back pain. Intervertebral fusion is one surgical method of alleviating back pain. In intervertebral fusion, two adjacent vertebral bodies are fused together by removing the affected intervertebral disc and inserting an implant that would allow for bone to grow between the two vertebral bodies to bridge the gap left by the disc removal. Another surgical method of relieving back pain is by corpectomy. In corpectomy, a diseased or damaged vertebral body along with the adjoining intervertebral discs are removed and replaced by a spinal implant that would allow for bone to grow between the closest two vertebral bodies to bridge the gap left by the spinal tissue removal.

A number of different implant materials and implant designs have been used for interbody fusion and for vertebral body replacement with varying success. Current implant materials used include metals, radiolucent materials including plastics, elastic and polymeric materials, ceramic, and allografts. Current implant designs vary from threaded cylindrical implants to rectangular cages with teeth-like protrusions.

For example, U.S. Pat. No. 5,782,919 to Zdeblick et. al. discloses an interbody fusion device which has a tapered body defining a hollow interior for receiving a bone graft or bone substitute material. Furthermore, the body of the device defines exterior threads for gripping the adjacent vertebrae and has a series of vascularization openings for promoting bony ingrowth. A variant on this design is shown in U.S. Pat. No. 4,961,740 to Ray et, al. The Ray patent illustrates a hollow, cylindrical fusion cage having a helical thread disposed on the outer surface of the cage with a plurality of holes leading to the hollow center between the threads.

U.S. Pat. No. 5,766,252 to Henry et. al. discusses a rectangular interbody spinal spacer that has vertically opposite upper and lower load bearing surfaces spaced apart a distance corresponding to the desired spacing. The rigid member has a wedge-shaped configuration with an ogival tip at the front end of the member.

While each of the foregoing prosthesis, address some problems relating to intervertebral disc replacements or vertebral body and intervertebral disc replacements, they present others. Thus, there is a need for an intervertebral implant whose design takes into consideration the anatomy and geometry of the intervertebral space sought to be filled by the intervertebral prosthesis as well as the anatomy and geometry of the end plates of the adjacent vertebral bodies. There is also a need for a spinal disc implant which integrates well with the vertebral bone tissue of the adjacent vertebral bodies between which the implant is to be inserted.

SUMMARY OF THE INVENTION

The present invention relates to an intervertebral implant for use when surgical fusion of vertebral bodies is indicated. The implant may be used to replace a diseased or damaged intervertebral disc or may be used to replace a diseased or damaged partial or complete vertebral body, or may be used to replace a diseased or damaged vertebral body and adjacent intervertebral discs.

In one embodiment, the implant comprises a body made from a biocompatible metal, radiolucent maternal, allograft, or resorbable material conforming substantially in size and shape with the end plates of the vertebrae, has a wedge-shaped profile, and has a central bore for receiving an osteoconductive material to promote the formation of new bone. The top and bottom surfaces may be flat planar surfaces, wedged, or curved surfaces. Preferably, the top and bottom surfaces mimic the topography of the vertebral end plates. The top and bottom surfaces each may have areas extending from an outer periphery of the implant to the central bore having a plurality of teeth for engaging the end plates of adjacent vertebra and each may also have areas extending from the outer periphery of the implant to the central bore that are substantially smooth for receiving a surgical instrument. The substantially smooth areas may extend in an anterior-posterior direction, a lateral direction, or may run in both directions. In addition, the substantially smooth area may run in an anterio-lateral direction.

The implant may have at least one channel on at least one side of the implant for receiving a surgical toot or instrument. This channel may also extend in at least an anterior-posterior direction, a lateral direction, or in both directions.

In another embodiment, instead of instrument receiving channels, the implant may have a threaded hole on the anterior, anterio-lateral, or lateral side of the implant for receiving a threaded arm of an Insertion tool.

In yet another embodiment, the implant may have a stackability feature wherein the implant is modular and comprises an upper endcap, and a lower endcap; or an upper endcap, a lower endcap, and at least one body portion.

BRIEF DESCRIPTION OF THE DRAWINGS

FIG. 22 is a top view of a lower endcap of the implant of FIG. 16A;

FIG. 23 is a bottom view of the lower endcap of FIG. 22;

FIG. 24 is a cross-sectional view taken at line A-A of the tower endcap of FIG. 22;

FIG. 25 is a cross-sectional view taken at line B-B of the tower endcap of FIG. 22;

FIG. 26 is a front or anterior view of the lower endcap of FIG. 22;

FIG. 52 is a top view of an alternate endcap of a sixth embodiment of the present invention;

FIG. 53 is a bottom view of the endcap of FIG. 52;

FIG. 54 is a cross-sectional view taken at line B-B of the endcap of FIG. 52;

FIG. 55 is a side or lateral view of the endcap of FIG. 52;

FIG. 56 is a front or anterior view of the endcap of FIG. 52;

DETAILED DESCRIPTION OF THE PREFERRED EMBODIMENTS

Figure 1:
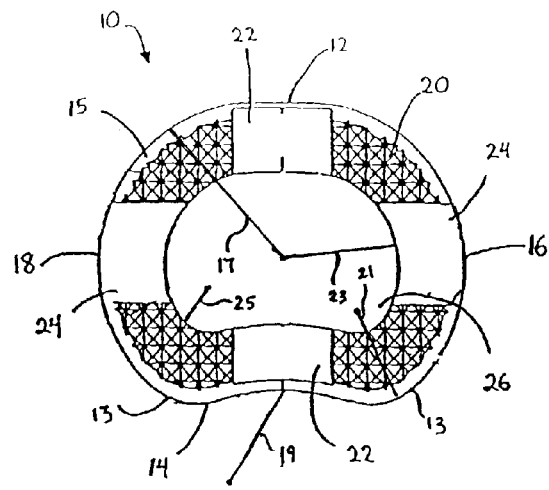
FIG. 1 is a top view of a first embodiment of the implant according to the present invention.

FIG. 1 shows a top view of a first embodiment of intervertebral spacer or implant 10 according to the present invention. Implant 10 has a generally kidney-bean shaped footprint which includes anterior side 12, posterior side 14, and first and second lateral sides 16, 18. Anterior side 12 and lateral sides 16, 18 are all substantially arcuate, preferably convex, in shape while posterior side 14 is substantially arcuate, preferably concave, in shape.

Implant 10 further includes central bore 26 which can be filled with bone growth inducing substances to allow bony ingrowth and to further assist in the fusion of the adjacent vertebrae and the implant. Central bore 26 has a generally kidney-bean shape that substantially conforms to the kidney-bean shaped footprint of implant 10. The radius of curvature 23 of the arcuate, preferably convex, sides of central bore 26 may be about 6.5 mm to about 8.5 mm, preferably about 7.5 mm, and the radius of curvature 25 of the areas between the preferably convex and concave sides are about 3 mm to about 3.4 mm, preferably about 3.2 mm.

In addition, implant 10, on its upper 15 and tower 30 surfaces, has sections or areas having teeth 20, spikes, or similar gripping structures to facilitate engagement of implant 10 with the end plates of the adjacent vertebra. The teeth may be pyramidal, saw toothed or other similar shapes. Ridges may also be used to facilitate gripping adjacent vertebrae. Implant 10 may also have sections or areas 22 or 24 or both which are essentially smooth and devoid of any protrusions. Sections 22, 24 are provided to assist the surgeon in implantation of the spacer as will be discussed below.

As mentioned above, implant 10 has a generally kidney-bean shaped footprint. This footprint is designed to conform in size and shape with the general perimeter and shape of the end plates of the vertebrae between which implant 10 is to be implanted thereby providing maximum support while avoiding the intravertebral foramen of the vertebral bodies. The intravertebral foramen or the spinal canal is the portion of the vertebral body that houses the spinal cord and nerve roots. Generally, a portion of the intravertebral foramen extends into the body portion or end plate portion of the vertebra. This portion of the intravertebral foramen, in effect, changes the perimeter of the body portion of the vertebra from substantially an oval shape to substantially a kidney-bean shape. Accordingly, the footprint of implant 10 is kidney-bean shaped to emulate the general shape and perimeter of the body portion of the adjacent vertebrae.

Figure 2:
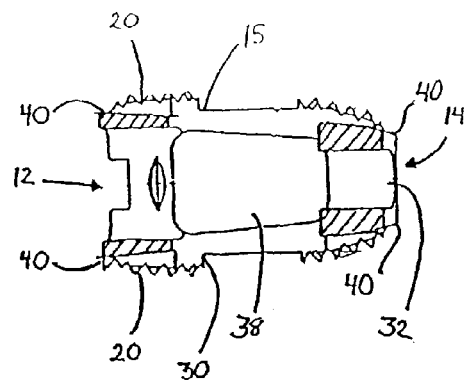
FIG. 2 is a cross-sectional side view of the implant of FIG. 1.
Figure 4:
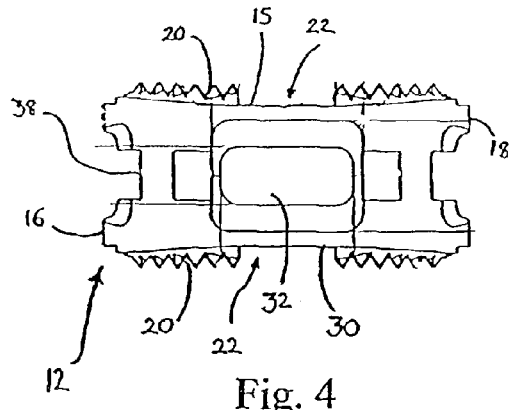
FIG. 4 is a front or anterior view of the implant of FIG. 1.

Implant 10 preferably also has a generally wedge-shaped, side-view profile that is designed to restore the natural curvature or lordosis of the spine after the affected disc or affected vertebral body and adjoining discs have been removed. As shown in FIGS. 2 and 4, this wedge shape results from a gradual increase in height from anterior side 12 followed by a decrease in height as posterior side 14 is approached. The implant has a generally constant height from lateral side 16 to lateral side 18. In another preferred embodiment, the implant may have a gradual increase in height followed by a gradual decrease in height from lateral side 16 to lateral side 18. The substantially convex curvature of upper surface 15 and tower surface 30 change the height of implant 10 in the anterior to posterior direction. In another preferred embodiment, the substantially convex curvature of upper surface 15 and lower surface 30 change the height of implant 10 in the lateral direction. Implant 10 preferably has the greatest height generally midway between anterior side 12 and the center of implant 10. In an exemplary embodiment, upper surface 15 and lower surface 30 may also be flat planar surfaces or flat angled surfaces. Alternatively, the upper surface 15 and lower surface 30 may be substantially curved surfaces, preferably shaped to mimic the topography of the vertebral end plates.

In order to facilitate insertion of implant 10, posterior side 14 and anterior side 12 transition to upper and lower surfaces 15, 30 with rounded edges 40. Rounded edges 40 may enable implant 10 to slide between the end plates while minimizing the necessary distraction of the end plates. In a preferred embodiment, rounded edges 40 have a radius of curvature ranging from about 0.75 mm to 1.75 mm, but preferably is about 1.25 mm. In another preferred embodiment, rounded edges 40 may extend around the periphery of implant 10. Rounded edges 40 may also be used as a means to clean the edges of the implant 10 by eliminating any half or partial teeth located on or near the edge of the implant 10.

Figure 3:
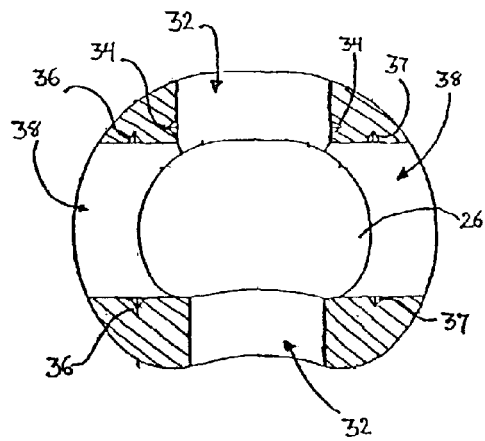
FIG. 3 is an axial cross-sectional view of the implant of FIG. 1.

As shown in FIG. 2 and FIG. 3, channel 32 runs through implant 10 from anterior side 12 through central bore 26 to posterior side 14. Channel 32 is sized to receive a surgical instrument such as an inserter for implantation of implant 10. In addition, located along the side of channel 32, near anterior side 12, are retaining grooves 34 which further assist with coupling the implantation instrument to implant 10. Using the implantation instrument with channel 32 and retaining grooves 34, implant 10 can be inserted in an anterior approach where posterior end 14 is the first side to be introduced to the intervertebral space.

Extending from a first lateral side 16 to a second lateral side 18 may be a second instrument receiving channel 38. Channel 38 is also sized to receive a surgical instrument such as an inserter for implantation of implant 10 and has retaining grooves 36 and 37 to further assist with coupling the implantation instrument to implant 10. Using the implantation instrument with channel 38 and retaining grooves 36, implant 10 can be inserted in a lateral approach where lateral side 16 is the first side to be introduced into the intervertebral space. Alternatively, using the implantation instrument with channel 38 and retaining grooves 37, implant 10 can be inserted in a lateral approach where lateral side 18 is the first side to be introduced into the intervertebral space.

Although spinal spacer insertion instruments are well known in the art, an inserter used with implant 10 may be modified to optionally include releaseable engaging members configured and dimensioned to mate with retaining grooves 34, 36, 37 to further assist with holding the implant during the insertion and installation procedure.

As can be seen in FIGS. 2 and 3, channel 32 is shown extending the entire length of the lateral sides 16, 18 of the implant 10. However, in an exemplary embodiment, channel 32 may extend only a portion of the length of lateral sides 16,18, or may extend the length of only one of the lateral sides 16, 18. Likewise, channel 38 may extend only a portion of the length of sides 12, 14 or may extend along one of the sides 12, 14.

Figure 4A:
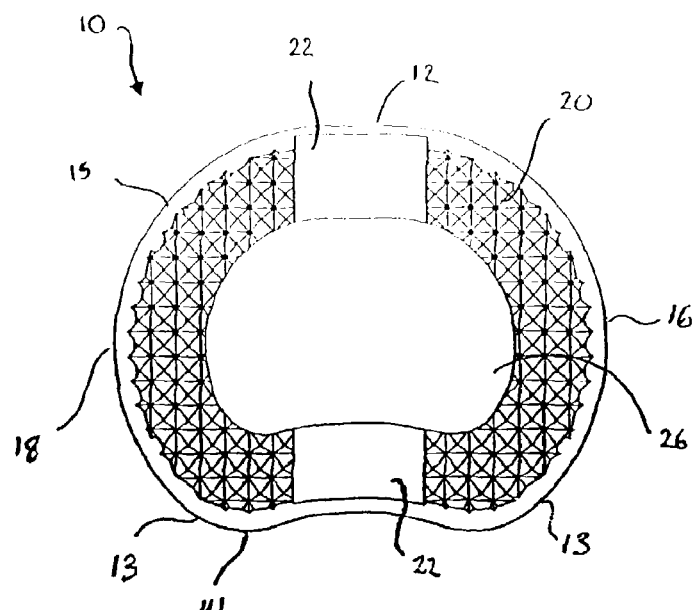
FIG. 4A is a top view of a another embodiment of the implant of FIG. 1.
Figure 4B:
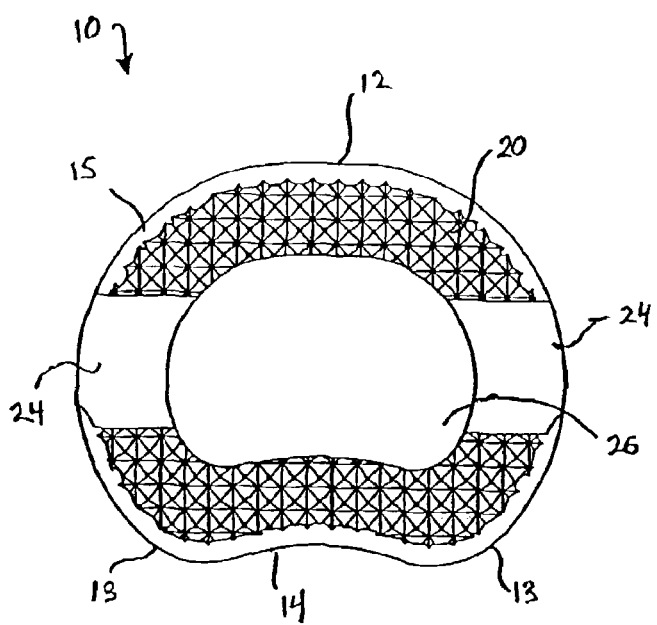
FIG. 4B is a top view of a another embodiment of the implant of FIG. 1.

To further assist with the insertion and implantation of implant 10, implant 10 has areas 22 and 24, located on the upper 15 and lower 30 surface of implant 10, which are substantially smooth and each are sized to receive an instrument such as a distractor, which is well known in the art. In this particular embodiment, area 22 extends in an anterior-posterior direction helping facilitate anterior implant insertion and area 24 extends in a transverse or lateral direction helping facilitate transverse implant insertion. Although in FIG. 1 area 22 is shown as extending along the entire longitudinal length of implant 10, from the perimeter edge of anterior side 12 to the perimeter edge of posterior side 14, area 22 may extend only partially along the longitudinal length of implant 10. The preceding is also applicable to area 24. Area 24 is shown to extend along the entire transverse length of implant 10, however, area 24 may extend only partially along the transverse length of implant 10. Furthermore, in an exemplary embodiment, only area 22, as shown in FIG. 4A, or only area 24, as shown in FIG. 4B, may be present on upper and lower surfaces 15, 30 of implant 10.

Implant 10 may be fabricated from pure titanium or an alloy thereof, preferably anodized to increase its biocompatibility by making it more inert. Implant 10 may also be fabricated from a radiolucent material, such as polyetheretherketone or polyetherketoneketone, and may include a radiopaque marker, such as a titanium alloy pin. The radiopaque marker may be located along any of the implant sides such as anterior side 12, posterior side 14 or lateral sides 16, 18. By using a radiolucent material, the progression and status of the fusion can be tracked through the use of X-rays or similar devices while the radiopaque marker will indicate the position of the implant with respect to the adjacent vertebral bodies. Implant 10 may also be fabricated from other biocompatible materials, such as allografts, and/or other resorbable materials.

The dimensions of the implant 10 may vary depending on where in the spine the implant will be inserted. The vertebral bodies in the lumbar area of the spine, for example, are larger than the vertebral bodies in the thoracic area. Therefore, an implant intended for the thoracic region would be smaller than one for the lumbar region. Likewise, lower lumbar disc replacements would be larger than upper ones. A person of ordinary skill could adapt the basic dimensions of the implant to make them occupy the space formerly occupied by the particular vertebral disc which needs replacement. Implant 10 is generally sized for anterior, lateral, or anterio-lateral approaches where inserting the implant around the spinal cord or spinal dural sac is not necessary as in a posterior approach. An exemplary embodiment of implant 10 may have a width (extending from anterior side 12 to posterior side 14) ranging from 15 mm-40 mm, but preferably about 22-26 mm, and most preferably about 24 mm, and a length (extending from lateral side 16 to lateral side 18) ranging from 20 mm-50 mm, but preferably about 28-32 mm, and most preferably about 30 mm. In addition, in an exemplary embodiment, the height of implant 10, measure as the distance between upper surface 15 and lower surface 30, when used as an intervertebral spacer, may be in the range of about 5 mm to about 25 mm. When using implant 10 as a corpectomy device, the height of implant 10 may range from about 17 mm to about 100 mm. Furthermore, in an exemplary embodiment, the radius of curvature 19 (shown in FIG. 1) of the concave and the radius of curvature 17 (shown in FIG. 1) of the convex sides may range from about 8 mm to about 30 mm, but preferably are about 13 mm. The radius of curvature 21 (shown in FIG. 1) of transition areas 13 which connect concave side 14 with convex sides 16, 18 may be about 4 mm to about 8 mm, but preferably are about 6 mm. Also, in an exemplary embodiment, the radius of curvature of the upper and lower surfaces of implant 10 from anterior side 12 to posterior side 14 may range from about 40 mm to about 100 mm, but preferably about 50 mm. The upper and lower surfaces 15, 30 are preferably flat between lateral sides 16, 18.

Figure 5:
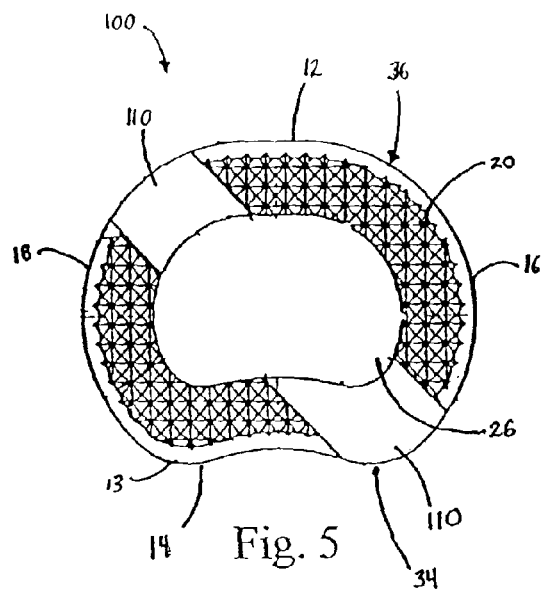
FIG. 5 is a top view of a second embodiment of the present invention.
Figure 6:
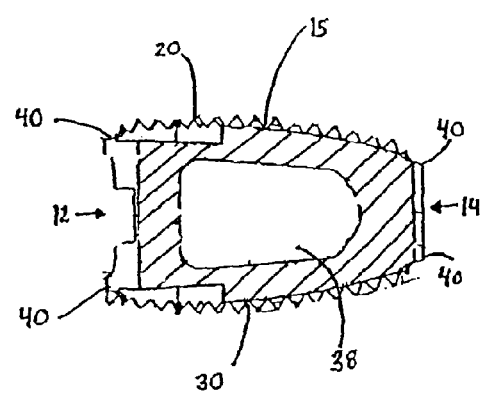
FIG. 6 is a cross-sectional side view of the implant of FIG. 5.
Figure 7:
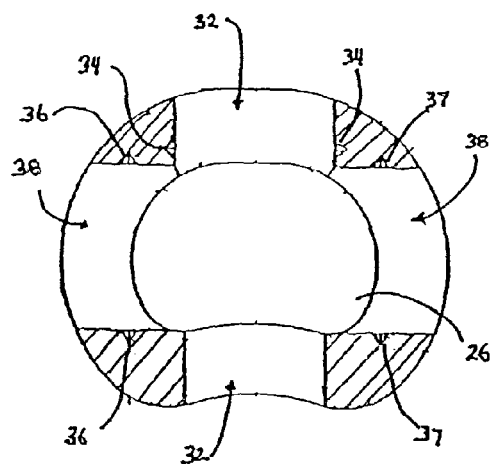
FIG. 7 is an axial cross-sectional view of the implant of FIG. 5.
Figure 8:
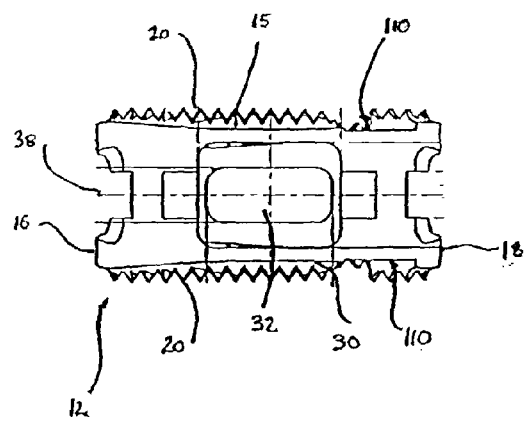
FIG. 8 is a front or anterior view of the implant of FIG. 5.

FIG. 5 shows a top view of a second embodiment of an implant 100. In general, most of the structure of implant 100 is similar or comparable to the structure of implant 10. Accordingly, the equivalent structures of implant 100 have been numbered the same as implant 10 and discussion of the similar components and features is not believed necessary. In this particular embodiment, located on upper surface 15 and lower surface 30 of implant 100, is area 110. Area 110 extends simultaneously in a longitudinal and lateral direction diagonally across implant 110 to facilitate anterio-lateral implant insertion. Although in FIG. 5 area 110 is shown as extending along the entire length of implant 100, area 110 may extend only partially along the length of implant 100.

Similar to implant 10 discussed above, implant 100 has the two sets of instrument receiving channels to increase surgical flexibility when inserting implant 100 and to facilitate the insertion process by creating more surgical insertion alternatives. In the case of an anterio-lateral insertion, either channel 38 with retaining grooves 36 and 37 may be used or channel 32 with retaining grooves 34 may be used.

Figure 9:
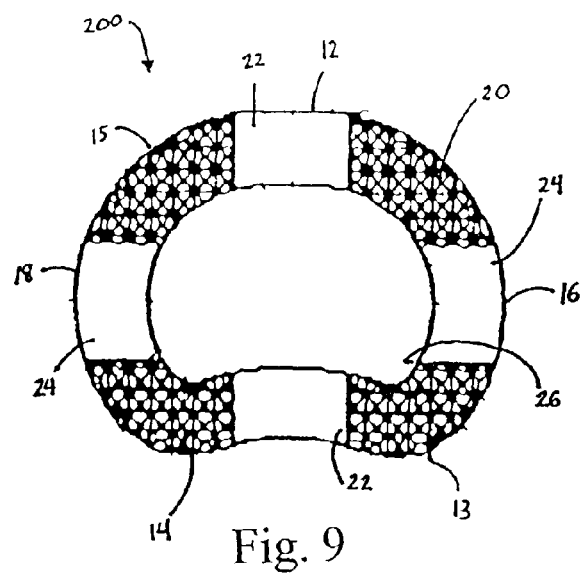
FIG. 9 is a top view of a third embodiment of the present invention.

FIG. 9 shows a top view of a third embodiment of an implant 200. In general, most of the structure of implant 200 is similar or comparable to the structure of implant 10. Accordingly, the equivalent structures of implant 200 have been numbered the same as implant 10 and discussion of the similar components and features is not believed necessary. In this particular embodiment, instead of having instrument receiving channels, implant 200 has threaded bores 210, 212. Threaded bores 210, 212 are sized to receive an implantation instrument such as a threaded inserter.

Figure 10:
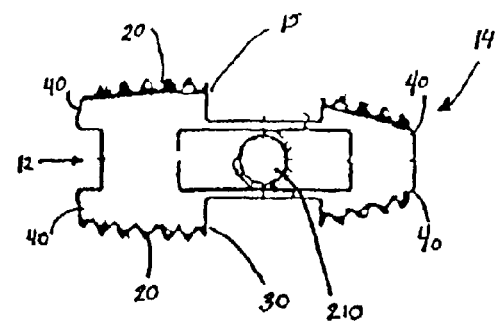
FIG. 10 is a side view of the implant of FIG. 9.
Figure 11:
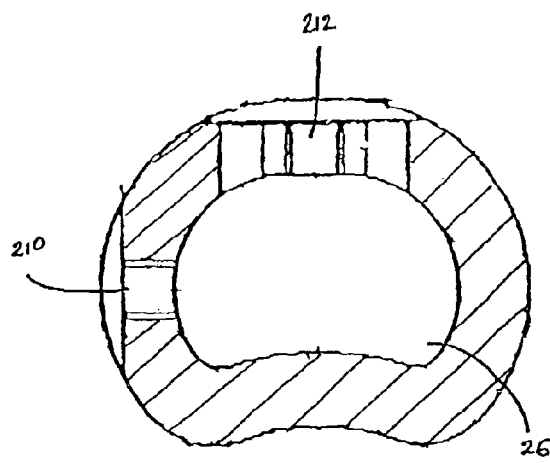
FIG. 11 is an axial cross-sectional view of the implant of FIG. 9.
Figure 12:
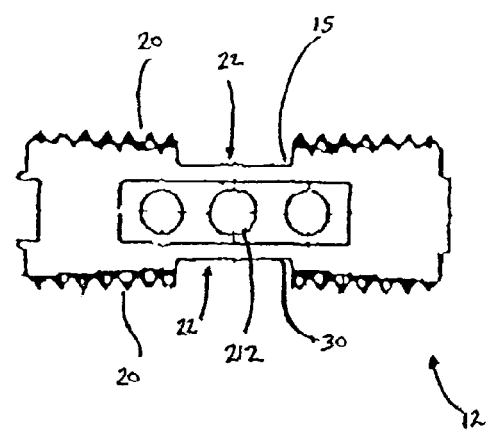
FIG. 12 is a front or anterior view of the implant of FIG. 9.

As can best be seen in FIGS. 10 and 11, threaded bore 210 is located on lateral side 18. This location allows for insertion of implant 200 in a lateral fashion. Although, threaded bore 210 is located on lateral side 18, it may also be located on lateral side 16. This location also allows for insertion of implant 200 in a lateral direction. FIGS. 11 and 12 show threaded bore 212 which is located on anterior side 12 of implant 200. This location allows for insertion of implant 200 in an anterior direction with posterior side 14 being the first side to be introduced to the intervertebral space.

Figure 13:
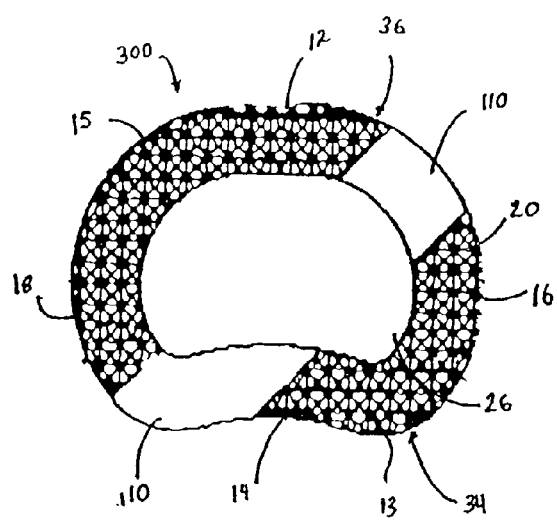
FIG. 13 is a top view of a fourth embodiment of the present invention.
Figure 14:
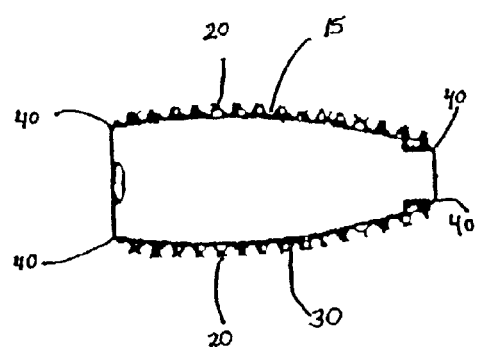
FIG. 14 is a side view of the implant of FIG. 13.

FIG. 13 shows a top view of a fourth embodiment of an implant 300. In general, most of the structure of implant 300 is similar or comparable to the structure of implant 100. Accordingly, the equivalent structures of implant 300 have been numbered the same as implant 100 and discussion of the similar components and features is not believed necessary. In this particular embodiment, instead of having instrument receiving channels, implant 300 has threaded bore 310. Threaded bore 310, is sized to receive an implantation instrument such as a threaded inserter.

Figure 15:
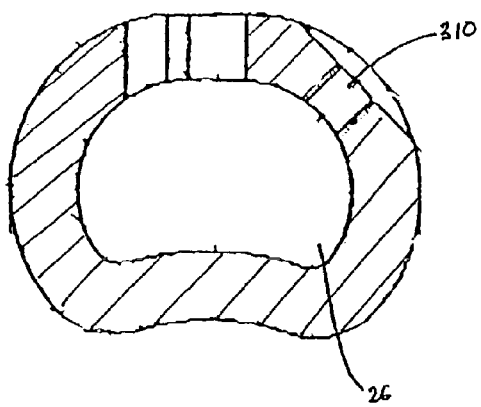
FIG. 15 is an axial cross-sectional view of the implant of FIG. 13.
Figure 16:
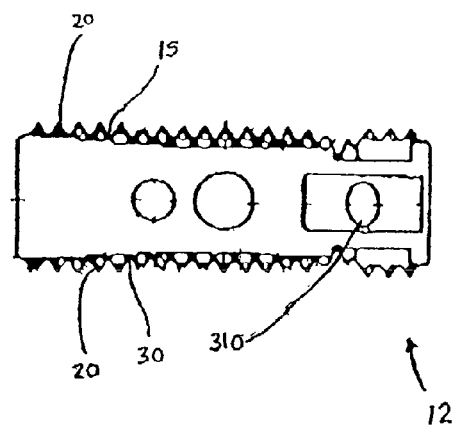
FIG. 16 is a front or anterior view of the implant of FIG. 13.

As can best be seen in FIGS. 15 and 16, threaded bore 310 is located on an anterio-lateral side (between anterior side 12 and lateral side 16) of implant 300. This location allows for insertion of implant 200 in an anterio-lateral fashion. Although, threaded bore 310 is located on an anterio-lateral side (between anterior side 12 and lateral side 16), it can also be located on an opposite anterio-lateral side (between anterior side 12 and lateral side 18) also allowing for an anterio-lateral implantation.

Figure 16A:
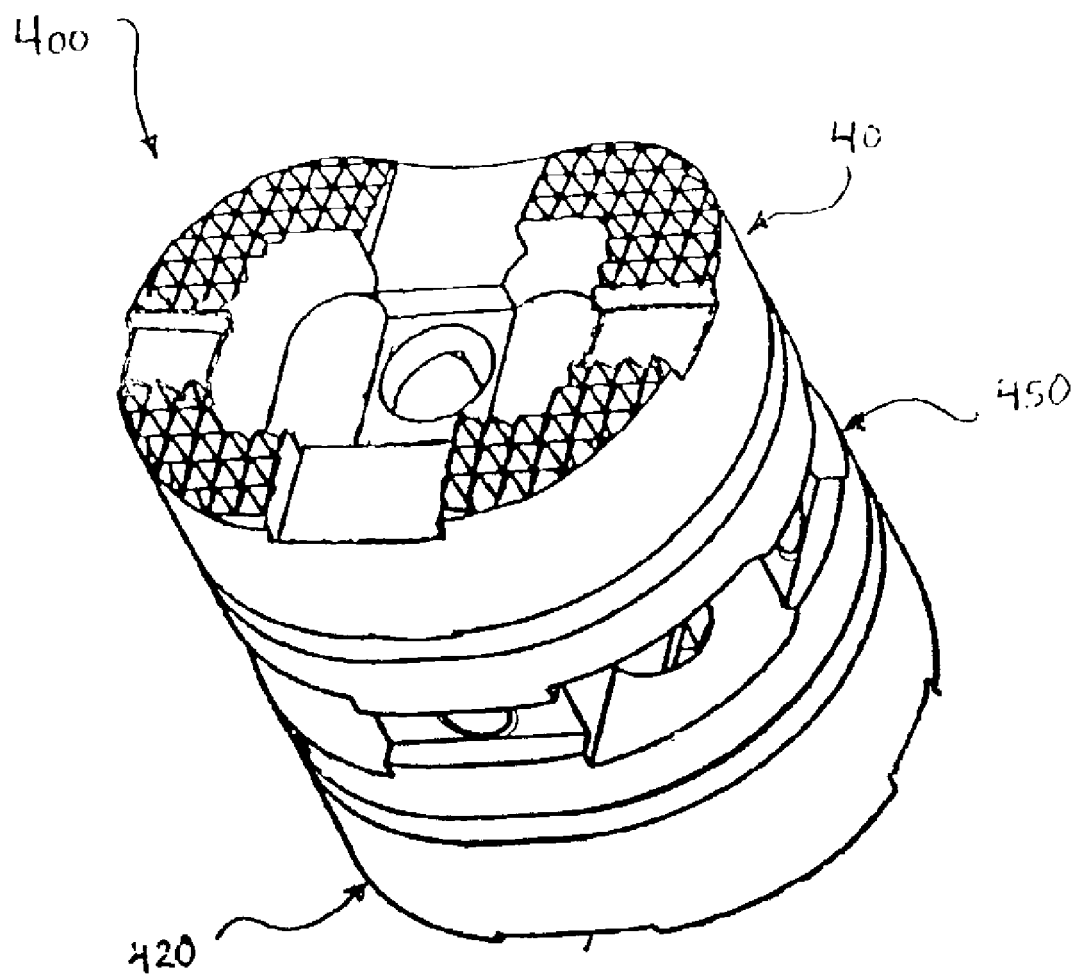
FIG. 16A is a perspective view of a fifth embodiment of the present invention.
Figure 17:
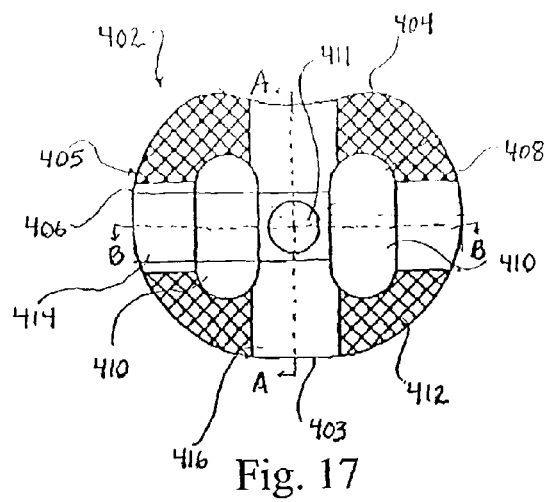
FIG. 17 is a top view of an upper endcap of the implant of FIG. 16A.

In a fifth embodiment, implant 400 is similar to the previously disclosed embodiment but now has a stackability feature. As will be further explained below, implant 400 includes an upper endcap and a lower endcap which may be stacked to form the spacer or implant. As shown in FIG. 16A, implant 400 may also include at least one body portion which may be stacked between the upper endcap and the lower endcap to form the spacer or implant. FIG. 17 shows a top view of upper endcap 402 of implant 400. Upper endcap 402 has a generally kidney-bean shaped footprint which includes anterior side 403, posterior side 404, and first and second lateral sides 406, 408. Anterior side 403 and lateral sides 406, 408 are alt substantially arcuate, preferably convex, in shape while posterior side 404 is substantially arcuate, preferably concave, in shape.

Figure 18:
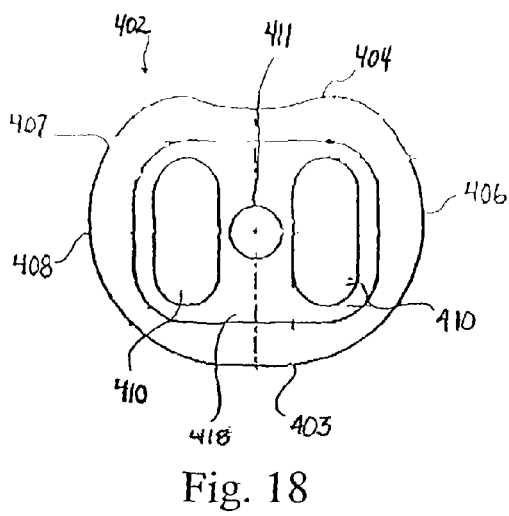
FIG. 18 is a bottom view of the upper endcap of FIG. 17.
Figure 21:
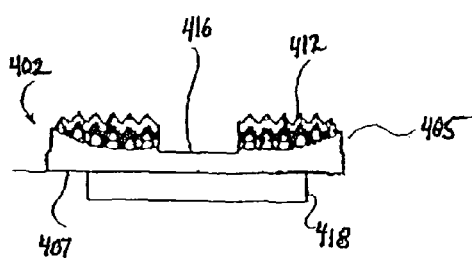
FIG. 21 is a front or anterior view of the upper endcap of FIG. 17.
Figure 27:
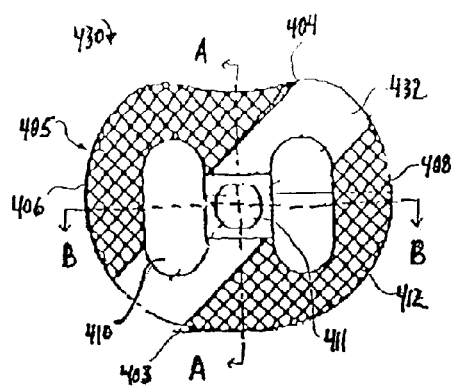
FIG. 27 is a top view of an alternate upper endcap of a fifth embodiment of the present invention.
Figure 28:
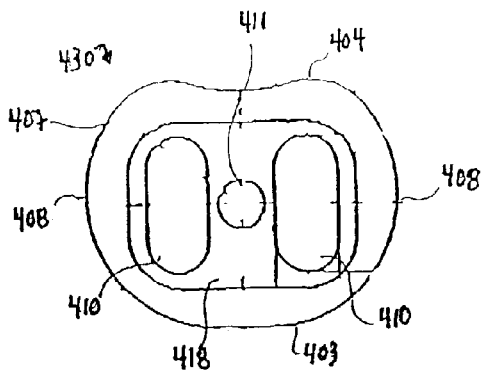
FIG. 28 is a bottom view of the upper endcap of FIG. 27.
Figure 29:
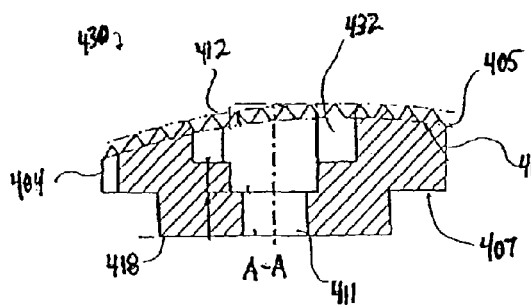
FIG. 29 is a cross-sectional view taken at line A-A of the upper endcap of FIG. 27.
Figure 30:
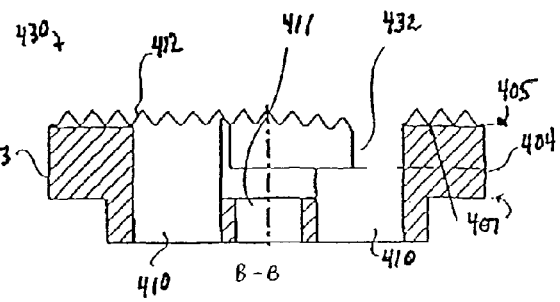
FIG. 30 is a cross-sectional view taken at line B-B of the upper endcap of FIG. 27.
Figure 31:
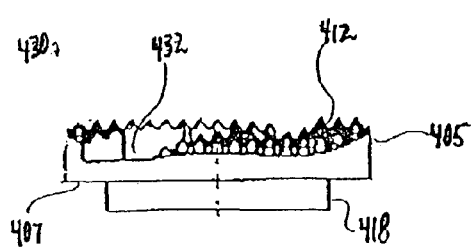
FIG. 31 is a front or anterior view of the upper endcap of FIG. 27.

As shown in FIGS. 17-20, upper endcap 402 also includes two elongated bores 410 which can be filled with bone growth inducing substances to allow bony ingrowth and to further assist in the fusion of the adjacent vertebrae. Upper endcap 402 further includes a central bore 411 for receiving a fastening member such as a screw. In addition upper endcap 402, on its upper surface 405, has sections or areas having teeth 412 or similar gripping means to facilitate engagement of implant 400 with the end plates of the adjacent vertebra, and has sections or areas 414, 416 which are substantially smooth and devoid of any protrusions. Although in FIG. 17 sections 414, 416 are shown as extending along the entire length of upper endcap 402, from perimeter edge to perimeter edge, sections 414, 416 may extend only partially along the length of upper endcap 402. Sections 414, 416 are provided to assist the surgeon in anterior or lateral implantation of the implant as was discussed above with respect to sections 22, 24. As can be seen in FIGS. 18 and 21, upper endcap 402 has a generally rectangular protrusion 418 configured and dimensioned to interface and mate with a recess portion of the implant body or with the lower endcap. While protrusion 418 has been shown and described as generally rectangular, it can be appreciated that protrusion 418 can be any shape desired. A lower surface 407 surrounds the protrusion 418. Lower surface 407 is illustrated as surrounding and encircling completely protrusion 418, but it can be appreciated that lower surface 407 may only partially surround protrusion 418.

Figure 19:
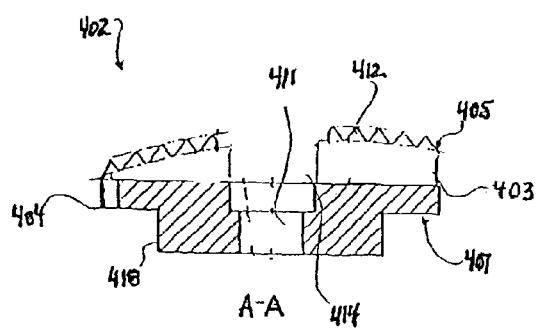
FIG. 19 is a cross-sectional view taken at line A-A of the upper endcap of FIG. 17.
Figure 20:
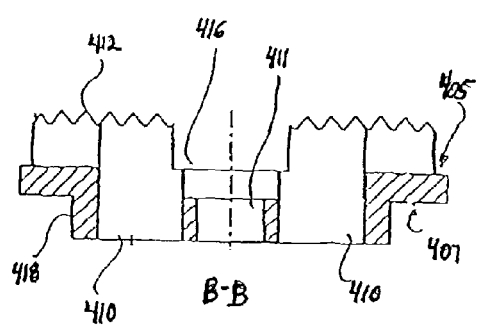
FIG. 20 is a cross-sectional view taken at line B-B of the upper endcap of FIG. 17.

Upper endcap 402 may have a generally wedge-shaped, side profile that is designed to restore the natural curvature or lordosis of the spine after the affected disc or affected vertebral body and adjoining discs have been removed. As shown in FIG. 19, this wedge shape results from a gradual increase in height from anterior side 403 followed by a decrease in height as posterior side 404 is approached. The substantially convex curvature of upper surface 405 changes the height of implant 400 along its width. In an exemplary embodiment, upper surface 405 may also be a flat planar surface, a flat angled surface, or a substantially curved surface, preferably shaped to mimic the topography of the adjacent vertebral end plates. The radius of curvature for upper surface 405 may be the same as described for the one-piece implant described earlier.

FIG. 22 shows a top view of a lower endcap 420. In general, most of the structure of endcap 420 is similar or comparable to the structure of endcap 402. Accordingly, the equivalent structures of endcap 420 have been numbered the same as endcap 402 and discussion of the similar components and features is not believed necessary. As discussed with endcap 402, endcap 420 also has a generally kidney-bean shaped footprint which includes anterior side 403, posterior side 404, and first and second lateral sides 406, 408. Anterior side 403 and lateral sides 406, 408 are all substantially arcuate, preferably convex, in shape while posterior side 404 is substantially arcuate, preferably concave, in shape. As can be seen in FIGS. 37-41, on lower surface 407, lower endcap 420 has a shoulder 424 defining a cavity 422 configured and dimensioned to interface and mate with a portion of the implant body. Shoulder 424 has been shown as surrounding cavity 422 entirely, but it should be appreciated that shoulder 424 may only partially surround cavity 422.

Turning now to FIGS. 27-31, an alternative embodiment of upper endcap 430 can be seen. In general, most of the structure of upper endcap 430 is similar or comparable to the structure of upper endcap 402. Accordingly, the equivalent structures of upper endcap 430 have been numbered the same as upper endcap 402 and discussion of the similar components and features is not believed necessary. In this particular embodiment, located on upper surface 405 of upper endcap 430, is area 432. Area 432 extends simultaneously in a longitudinal and lateral direction diagonally across upper endcap 430 to facilitate anterio-lateral implant insertion. Although in FIGS. 27-31, area 432 is shown as extending along the entire length of upper endcap 430, area 432 may extend only partially along the length of upper endcap 430.

Figure 32:
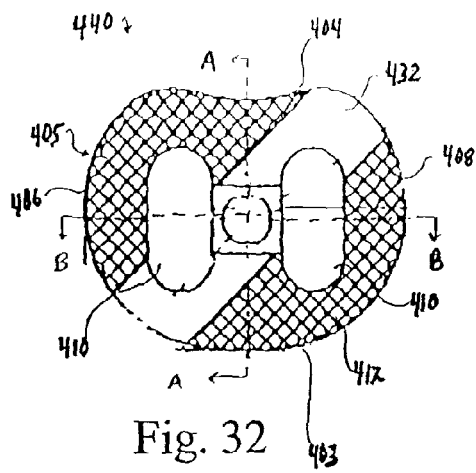
FIG. 32 is a top view of an alternate lower endcap of a fifth embodiment of the present invention.
Figure 33:
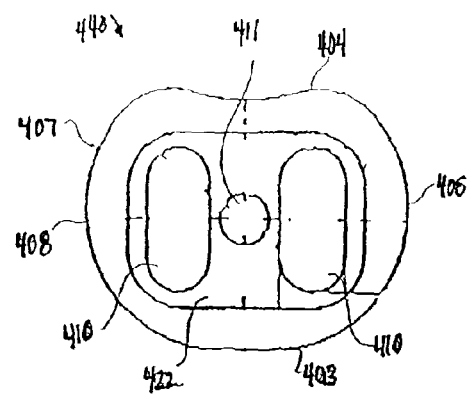
FIG. 33 is a bottom view of the lower endcap of FIG. 32.
Figure 34:
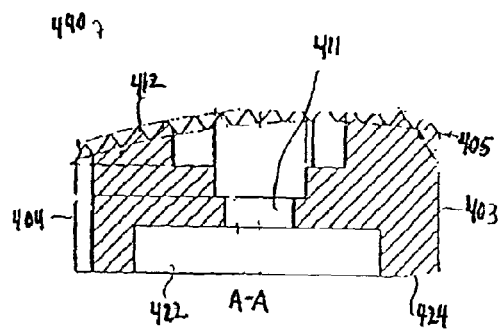
FIG. 34 is a cross-sectional view taken at line A-A of the lower endcap of FIG. 32.
Figure 35:
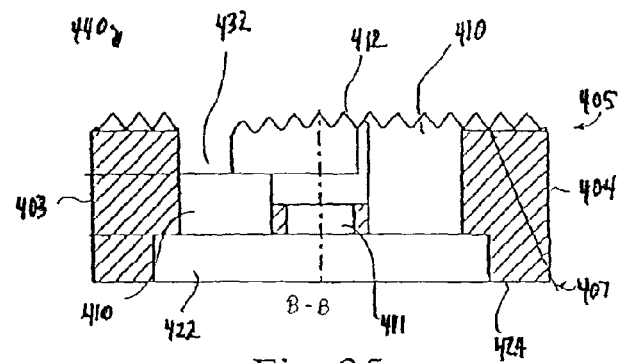
FIG. 35 is a cross-sectional view taken at line B-B of the tower endcap of FIG. 32.
Figure 36:
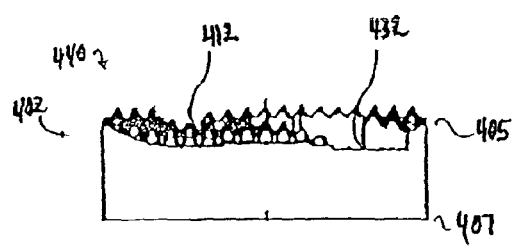
FIG. 36 is a front or anterior view of the lower endcap of FIG. 32.

FIG. 32 shows a top view of a lower endcap 440. In general, most of the structure of lower endcap 440 is similar or comparable to the structure of lower endcap 420. Accordingly, the equivalent structures of lower endcap 440 have been numbered the same as lower endcap 420 and discussion of the similar components and features is not believed necessary. As can be seen in FIGS. 32-36, located on lower surface 405 of lower endcap 440, is area 432. Area 432 extends simultaneously in a longitudinal and lateral direction diagonally across lower endcap 440 to facilitate anterio-lateral implant insertion. Although in FIGS. 32-35, area 432 is shown as extending along the entire length of lower endcap 440, area 432 may extend only partially along the length of upper endcap 440.

Figure 37:
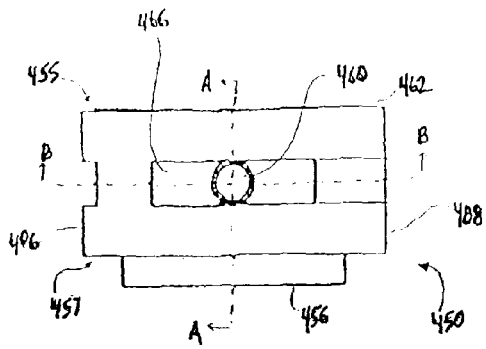
FIG. 37 is a front or anterior view of a body portion of the implant of FIG. 16A.
Figure 38:
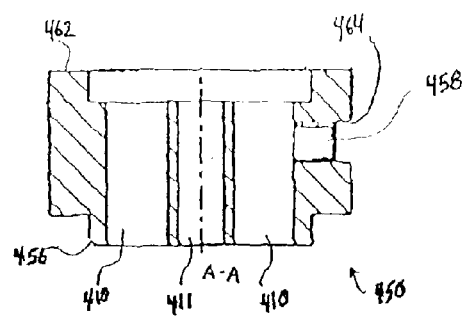
FIG. 38 is a cross-sectional view taken at line A-A of the body portion of FIG. 37.
Figure 39:
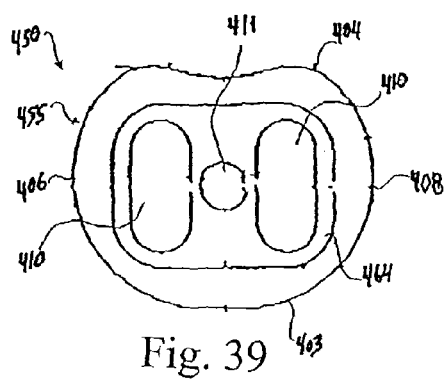
FIG. 39 is a top view of the body portion of FIG. 37.
Figure 40:
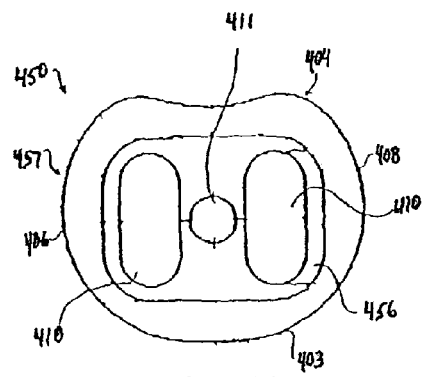
FIG. 40 is a bottom view of the body portion of FIG. 37.

FIG. 37 shows a front or anterior view of a body portion 450. In general, some of the structure of body portion 450 is similar or comparable to the structure of upper and lower endcaps 402, 420, 430, 440. Accordingly, the equivalent structures of body portion 450 have been numbered the same as upper and lower endcaps 402, 420, 430, 440 and discussion of the similar components and features is not believed necessary. As can be seen in FIGS. 37-40, body portion 450 has a generally kidney-bean shape footprint. Located on upper surface 455, body portion 450 has a shoulder 462 defining a cavity 464 and located on lower surface 457, body portion 450 has a generally rectangular protrusion 456. While shoulder 462 is shown as completely enclosing and surrounding cavity 464, shoulder 462 may only partially surround cavity 464. Likewise, lower surface 457 is shown as completely surrounding protrusion 456, but it can be appreciated that lower surface 457 may only partially surround protrusion 456. Shoulder 462 and cavity 464 are configured and dimensioned to interface and mate with either rectangular protrusion 418 of upper endcaps 402, 430 or rectangular protrusion 456 of another body portion 450. Protrusion 456 of body portion 450 is configured and dimensioned to interface and mate with either cavity 422 of lower end plates 420, 440 or cavity 464 of another body portion 450. Again, while the protrusions have been described as rectangular, any geometric shape is contemplated.

As mentioned above, implant 400 is a stackable implant comprising an upper endcap 402, 430, a lower endcap 420, 440, and, if necessary, at least one body portion 450. It is also possible for implant 400 to include an upper endcap 402, 430 and a lower endcap 420, 440. The modularity of implant 400, allows implant 400 to have a variable height, thereby allowing a surgeon to create an implant sized to appropriately fit the surgical space. In use, once the implant height that will be needed for the surgical procedure is determined, the desired implant can be created from the endcaps and, if necessary, one or more body portions. If a smaller implant is needed, implant 400 may comprise upper endcap 402, 430, and lower endcap 420, 440. If a larger implant is needed, implant 400 may comprise upper endcap 402, 430, lower endcap 420, 440 and at least one body portion 450. Body portions 450 may be the same size or of various sizes. Upper and lower endcaps 402, 420, 430, 440 and body portion 450 are configured and dimensioned to mate with each other via an interference or similar fit. For further fixation of the endcaps and body portion together, a fixation screw may be threaded into central bore 411. Additional screws and bores my also be used.

Body portion 450 also may include channels 464, 466 or threaded bores 458, 460 for implantation of the assembled implant 400. Channel 464 runs anterior to posterior through body portion 450 from anterior side 403 to posterior side 404. Channel 464 is sized to receive a surgical instrument such as an inserter for implantation of implant 400. Using the implantation instrument, implant 400 can be inserted in a lateral approach where the contra-lateral side is the first side to be introduced into the intervertebral space. Alternatively, using the implantation instrument with channel 464, implant 400 may be inserted in a lateral approach where lateral side 408 is the first side to be introduced to the intervertebral space.

Extending from a first lateral side 406 to a second lateral side 408 may be a second instrument receiving channel 466 (not shown). Channel 466 is also sized to receive a surgical instrument such as an inserter for implantation of implant 400. Using the implantation instrument with channel 466, implant 400 may be inserted in an anterior approach where posterior end 404 is the first side to be introduced to the intervertebral space.

Although channel 464 is described as extending the entire length of the lateral sides 406, 408 of the implant 400, channel 464 may extend only a portion of the length of lateral sides 406, 408, or may extend the length of only one of the lateral sides 406, 408. Likewise, channel 466 may extend the length of one of the sides 403, 404 or may extend only a portion of the length of sides 403, 404.

Implant 400, instead of having instrument receiving channels, may have threaded bores 458, 460. Threaded bores 458, 460 are sized to receive an implantation instrument such as a threaded inserter.

Figure 41:
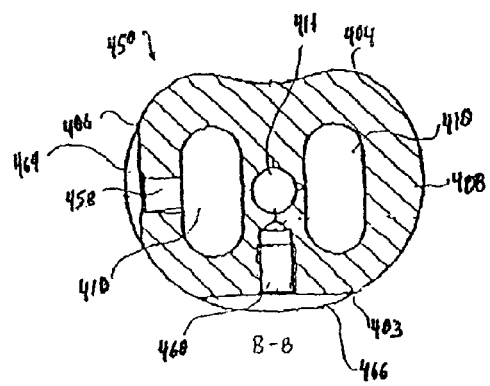
FIG. 41 is a cross-sectional view taken at line B-B of the body portion of FIG. 37.

As can best be seen in FIGS. 37 and 41, threaded bore 458 is located on lateral side 406. This location allows for insertion of implant 400 in a lateral fashion. Although, threaded bore 458 is located on lateral side 406, it may also be located on lateral side 408. This location also allows for insertion of implant 400 in a lateral direction. FIG. 41 shows threaded bore 460 which is located on anterior side 403 of implant 400. This location allows for insertion of implant 400 in an anterior direction with posterior side 404 being the first side to be introduced to the intervertebral space.

Figure 42:
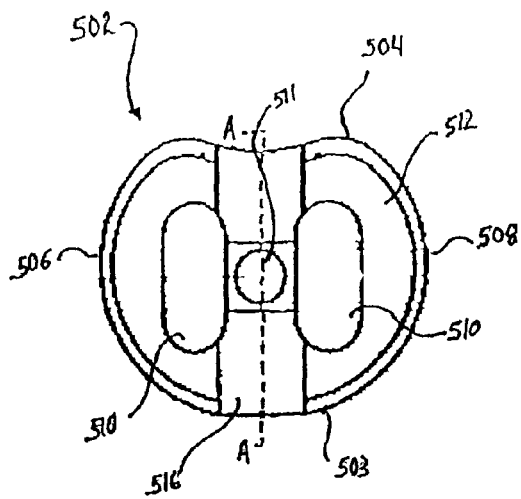
FIG. 42 is a top view of an endcap of a sixth embodiment of the present invention.

In a sixth embodiment, implant 500 is similar to the previously disclosed stackable embodiment, however implant 500 has a different coupling configuration for stacking. As will be further explained below, implant 500 includes a plurality of endcaps which may be stacked to form the spacer or implant. Implant 500 may also include at least one body portion which may be stacked between the endcaps to form the implant. FIG. 42 shows a top view of endcap 502 of implant 500. Endcap 502 has a generally kidney-bean shaped footprint which includes anterior side 503, posterior side 504, and first and second lateral sides 506, 508. Anterior side 503 and lateral sides 506, 508 are all substantially arcuate, preferably convex, in shape while posterior side 504 is substantially arcuate, preferably concave, in shape.

Figure 43:
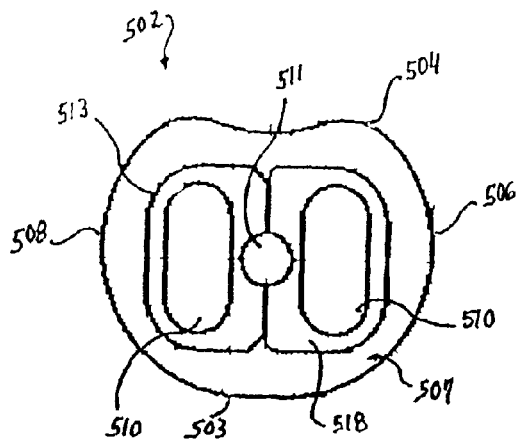
FIG. 43 is a bottom view of the endcap of FIG. 42.
Figure 46:
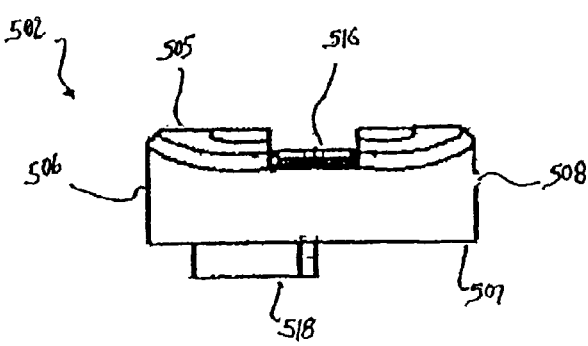
FIG. 46 is a front or anterior view of the endcap of FIG. 42.

As shown in FIGS. 42-46, endcap 502 also includes two elongated bores 510 which can be filled with bone growth inducing substances to allow bony ingrowth and to further assist in the fusion of the adjacent vertebrae. Endcap 502 further includes a central bore 511 for receiving a fastening member, such as a screw, sleeve, or nut. In addition, endcap 502, on its upper surface 505, has sections or areas having gripping structures 512 to facilitate engagement of implant 500 with the end plates of the adjacent vertebra, and has sections or areas 516 which are substantially smooth and devoid of any protrusions. Although in FIG. 42 sections 516 are shown as extending along the entire length of endcap 502, from perimeter edge to perimeter edge, sections 516 may extend only partially along the length of endcap 502. Sections 516 are provided to assist the surgeon in anterior or lateral implantation of the implant as was discussed above with respect to section 22. As can be seen in FIGS. 43 and 46, endcap 502 has a generally rectangular protrusion 518 configured and dimensioned to interface and mate with a recess portion of the implant body or another endcap. While protrusion 518 has been shown and described as generally rectangular, it can be appreciated that protrusion 518 can be any shape desired. A lower surface 507 surrounds the protrusion 518. Lower surface 507 is illustrated as surrounding and encircling completely protrusion 518, but it can be appreciated that lower surface 507 may only partially surround protrusion 518. Located proximate to protrusion 518, on lower surface 507, is a shoulder 515 defining a cavity 513. Cavity 513 is configured and dimensioned to interface and mate with a portion of the implant body or another endcap. Shoulder 515 has been shown as surrounding cavity 513 entirely, but it should be appreciated that shoulder 515 may only partially surround cavity 513. This different coupling configuration allows for interchangeability of the endcaps.

Figure 44:
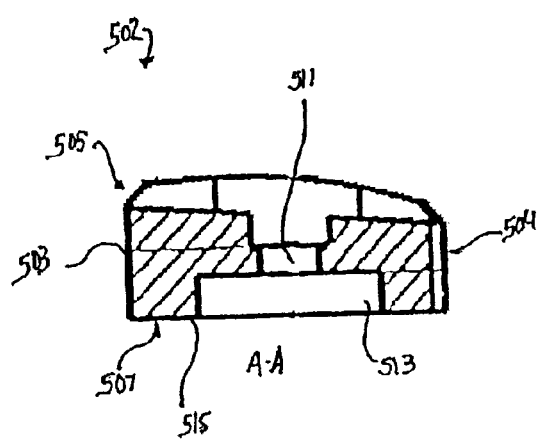
FIG. 44 is a cross-sectional view taken at line A-A of the endcap of FIG. 42.
Figure 45:
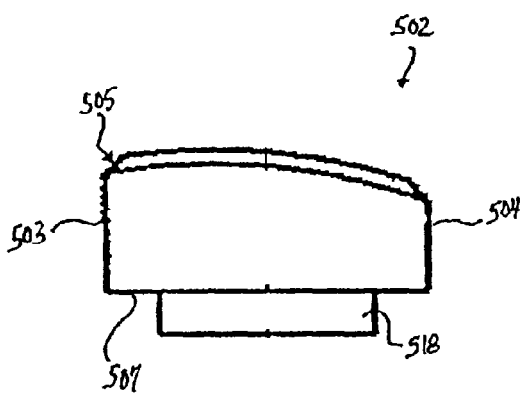
FIG. 45 is a side or lateral view of the endcap of FIG. 42.

Endcap 502 may have a generally wedge-shaped, side profile that is designed to restore the natural curvature or lordosis of the spine after the affected disc or affected vertebral body and adjoining discs have been removed. As shown in FIG. 44, this wedge shape results from a gradual increase in height from anterior side 503 followed by a decrease in height as posterior side 504 is approached. The substantially convex curvature of upper surface 505 changes the height of implant 500 along its width. In an exemplary embodiment, upper surface 505 may also be a flat planar surface, a flat angled surface, or a substantially curved surface, preferably shaped to mimic the topography of the adjacent vertebral end plates. The radius of curvature for upper surface 505 may be the same as described for the one-piece implant described earlier.

Figure 47:
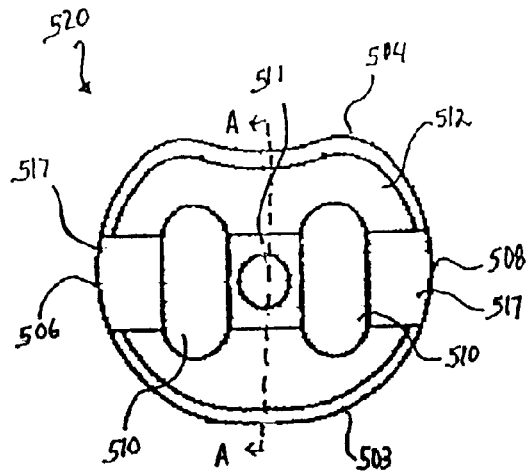
FIG. 47 is a top view of an alternate endcap of a sixth embodiment of the present invention.
Figure 48:
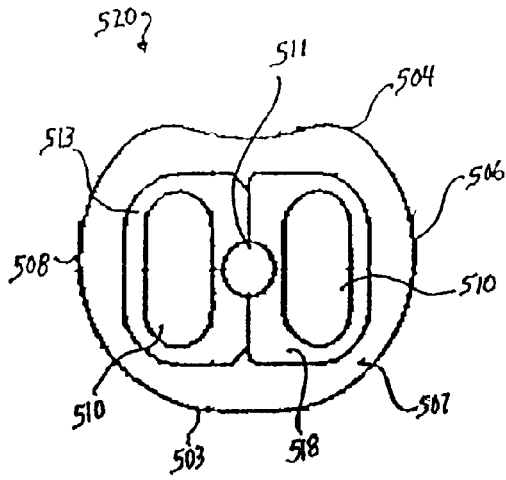
FIG. 48 is a bottom view of the endcap of FIG. 47.
Figure 51:
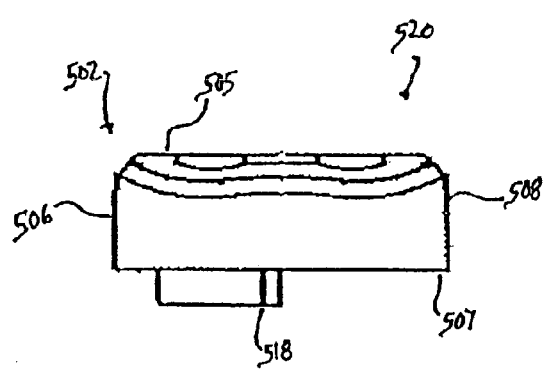
FIG. 51 is a front or anterior view of the endcap of FIG. 47.

FIG. 47 shows a top view of another endcap 520. In general, most of the structure of endcap 520 is similar or comparable to the structure of endcap 502. Accordingly, the equivalent structures of endcap 520 have been numbered the same as endcap 502 and discussion of the similar components and features is not believed necessary. As discussed with upper endcap 502, endcap 520 also has a generally kidney-bean shaped footprint which includes anterior side 503, posterior side 504, and first and second lateral sides 506, 508. Anterior side 503 and lateral sides 506, 508 are all substantially arcuate, preferably convex, in shape while posterior side 504 is substantially arcuate, preferably concave, in shape. As can be seen in FIGS. 47-51, endcap 520 also includes two elongated bores 510 which can be filled with bone growth inducing substances to allow bony ingrowth and to further assist in the fusion of the adjacent vertebrae. Endcap 520 further includes a central bore 511 for receiving a fastening member, such as a screw, sleeve or nut. In addition, endcap 520, on its upper surface 505, has sections or areas having gripping structures 512 to facilitate engagement of implant 500 with the end plates of the adjacent vertebra, and has sections or areas 517 which are substantially smooth and devoid of any protrusions. Although in FIG. 47 sections 517 are shown as extending along the entire length of endcap 520, from perimeter edge to perimeter edge, sections 517 may extend only partially along the length of endcap 520. Sections 517 are provided to assist the surgeon in transverse implantation of the implant as was discussed above with respect to section 24. As can be seen in FIGS. 48 and 51, endcap 520 has a generally rectangular protrusion 518 configured and dimensioned to interface and mate with a recess portion of the implant body or another endcap. While protrusion 518 has been shown and described as generally rectangular, it can be appreciated that protrusion 518 can be any shape desired. A lower surface 507 surrounds the protrusion 518. Lower surface 507 is illustrated as surrounding and encircling completely protrusion 518, but it can be appreciated that lower surface 507 may only partially surround protrusion 518. Located proximate to protrusion 518, on lower surface 507, is a shoulder 515 defining a cavity 513. Cavity 513 is configured and dimensioned to interface and mate with a portion of the implant body or another endcap. Shoulder 515 has been shown as surrounding cavity 513 entirely, but it should be appreciated that shoulder 515 may only partially surround cavity 513.

Figure 49:
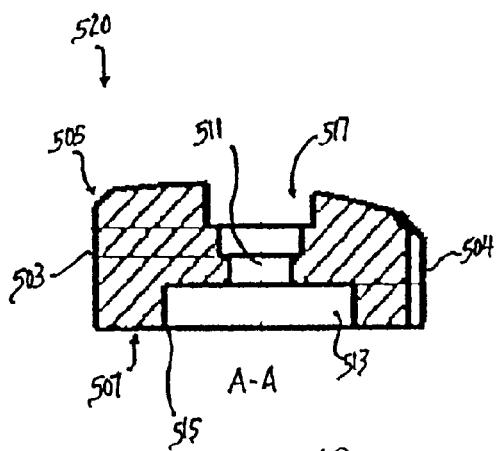
FIG. 49 is a cross-sectional view taken at line A-A of the endcap of FIG. 47.
Figure 50:
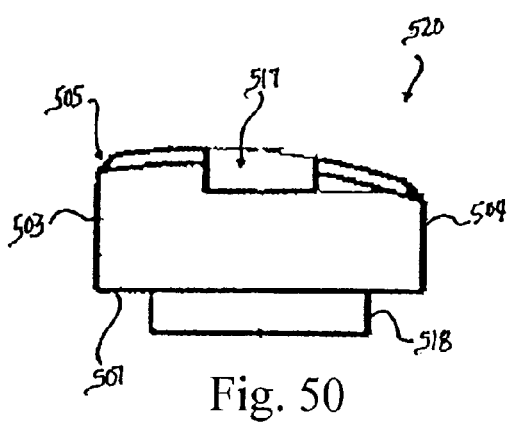
FIG. 50 is a side or lateral view of the endcap of FIG. 47.

Endcap 520 may have a generally wedge-shaped, side profile that is designed to restore the natural curvature or lordosis of the spine after the affected disc or affected vertebral body and adjoining discs have been removed. As shown in FIG. 49, this wedge shape results from a gradual increase in height from anterior side 503 followed by a decrease in height as posterior side 504 is approached. The substantially convex curvature of upper surface 505 changes the height of implant 500 along its width. In an exemplary embodiment, upper surface 505 may also be a flat planar surface, a flat angled surface, or a substantially curved surface, preferably shaped to mimic the topography of the adjacent vertebral end plates. The radius of curvature for upper surface 505 may be the same as described for the one-piece implant described earlier.

Turning now to FIGS. 52-56, an alternative embodiment of endcap 530 can be seen. In general, most of the structure of endcap 530 is similar or comparable to the structure of endcap 502. Accordingly, the equivalent structures of endcap 530 have been numbered the same as endcap 502 and discussion of the similar components and features is not believed necessary. In this particular embodiment, located on upper surface 505 of endcap 530, is area 519. Area 519 extends simultaneously in a longitudinal and lateral direction diagonally across endcap 530 to facilitate anterio-lateral implant insertion. Although in FIGS. 52-56, area 519 is shown as extending along the entire length of endcap 530, area 519 may extend only partially along the length of endcap 530.

Figure 57:
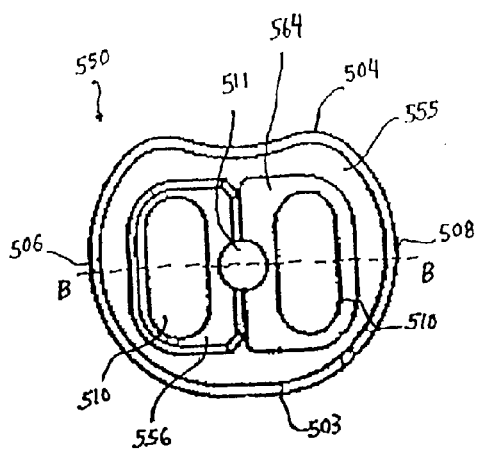
FIG. 57 is a top view of a body portion of a sixth embodiment of the present invention.
Figure 58:
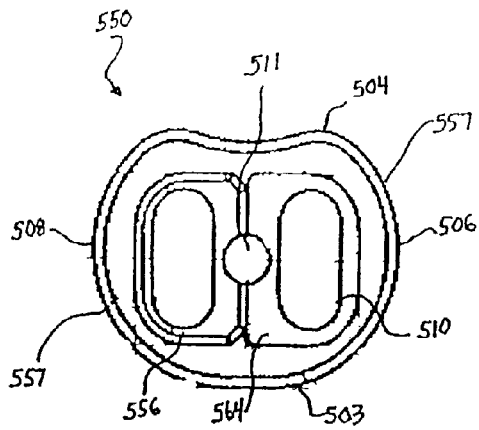
FIG. 58 is a bottom view of the body portion of FIG. 57.

FIG. 57 shows a top view of a body portion 550. In general, some of the structure of body portion 550 is similar or comparable to the structure of endcaps 502, 520, and 530. Accordingly, the equivalent structures of body portion 550 have been numbered the same as endcaps 502, 520, and 530 and discussion of the similar components and features is not believed necessary. As can be seen in FIGS. 57-62, body portion 550 has a generally kidney-bean shape footprint. Located on upper surface 555 and lower surface 557, body portion 550 has a shoulder 562 defining a cavity 564 and a generally rectangular protrusion 556. While shoulder 562 is shown as completely enclosing and surrounding cavity 564, shoulder 562 may only partially surround cavity 564. Likewise, upper surface 555 and lower surface 557 are shown as completely surrounding protrusions 556, but it can be appreciated that upper surface 555 and lower surface 457 may only partially surround protrusions 556. Shoulder 562 and cavity 564 are configured and dimensioned to interface and mate with either rectangular protrusion 518 of endcaps 502, 520, 530 or rectangular protrusion 556 of another body portion 550. Protrusion 556 of body portion 550 is configured and dimensioned to interface and mate with either cavity 513 of endcaps 502, 520, 530 or cavity 564 of another body portion 550. Again, while the protrusions have been described as rectangular, any geometric shape is contemplated.

As mentioned above, implant 500 is a stackable implant comprising two endcaps 502, 520, 530, and, if necessary, at least one body portion 550. The modularity of implant 500, allows implant 500 to have a variable height, thereby allowing a surgeon to create an implant sized to appropriately fit the surgical space. In use, once the implant height that will be needed for the surgical procedure is determined, the desired implant can be created from the endcaps and, if necessary, one or more body portions. If a smaller implant is needed, implant 500 may comprise two endcaps 502, 520, 530. If a larger implant is needed, implant 500 may comprise endcaps 502, 520, 530, and at least one body portion 550. Body portions 550 may be the same size or of various sizes. Endcaps 502, 520, 530, and body portion 550 are configured and dimensioned to mate with each other via an interference or similar fit. For further fixation of the endcaps or the endcaps and body portion together, a fixation screw may be threaded into central bore 511. Additional screws and bores my also be used.

Body portion 550 also may include channels 563, 566 and/or threaded bores 558, 560 for implantation of the assembled implant 500. Channel 563 runs anterior to posterior through body portion 550 from anterior side 503 to posterior side 504. Channel 563 is sized to receive a surgical instrument such as an inserter for implantation of implant 500. Using the implantation instrument, implant 500 can be inserted in a lateral approach where the contra-lateral side is the first side to be introduced into the intervertebral space. Alternatively, using the implantation instrument with channel 563, implant 500 may be inserted in a lateral approach where lateral side 508 is the first side to be introduced to the intervertebral space.

Extending from a first lateral side 506 to a second lateral side 508 may be a second instrument receiving channel 566. Channel 566 is also sized to receive a surgical instrument such as an inserter for implantation of implant 500. Using the implantation instrument with channel 566, implant 500 may be inserted in an anterior approach where posterior end 504 is the first side to be introduced to the intervertebral space.

Although channel 563 is described as extending the entire length of the lateral sides 506, 508 of the implant 500, channel 563 may extend only a portion of the length of lateral sides 506,508, or may extend the length of only one of the lateral sides 506, 508. Likewise, channel 566 may extend the length of one of the sides 503, 504 or may extend only a portion of the length of sides 503, 504.

Implant 500, instead of or in addition to having instrument receiving channels, may have threaded bores 558, 560. Threaded bores 558, 560 are sized to receive an implantation instrument such as a threaded inserter.

Figure 59:
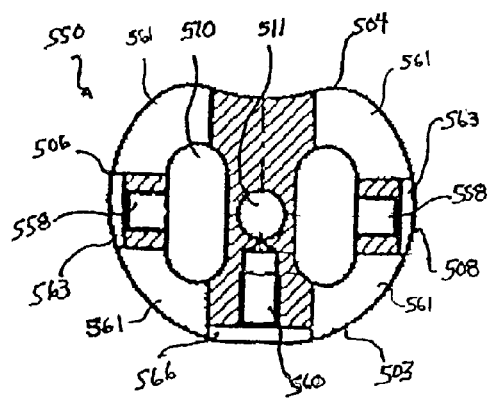
FIG. 59 is a cross-sectional view of the body portion of FIG. 57.
Figure 60:
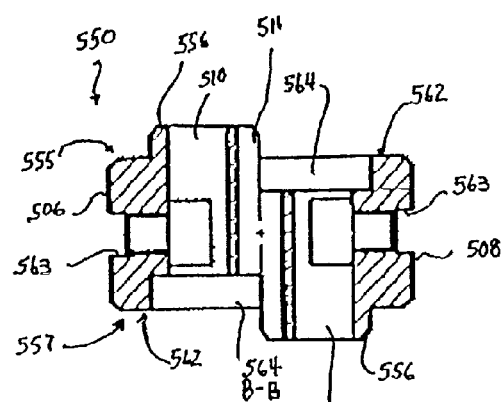
FIG. 60 is a cross-sectional view taken at line B-B of the body portion of FIG. 57.
Figure 61:
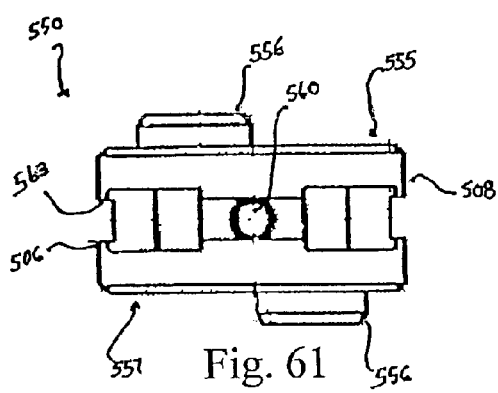
FIG. 61 is a front or anterior view of the body portion of FIG. 57.
Figure 62:
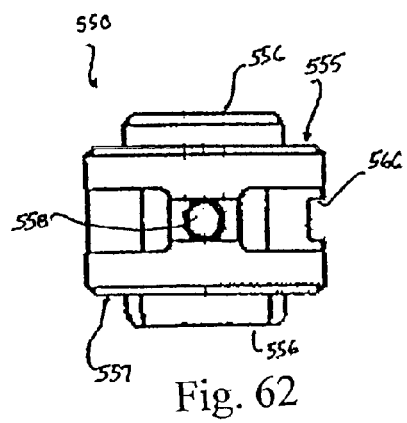
FIG. 62 is a side or lateral view of the body portion of FIG. 57.

As can best be seen in FIGS. 59, 61 and 62, threaded bore 558 is located on lateral sides 506, 508. This location allows for insertion of implant 500 in a lateral fashion. FIG. 59 shows threaded bore 560 which is located on anterior side 503 of implant 500. This location allows for insertion of implant 500 in an anterior direction with posterior side 504 being the first side to be introduced to the intervertebral space.

As can best be seen in FIG. 59, body portion 550 may also include openings 561, which preferably extend from the outer surface of body portion 550 to elongated bores 510. Openings 561 may be packed with bone growth inducing substances to further aid in the fixation and fusion of the implant.

Figure 63:
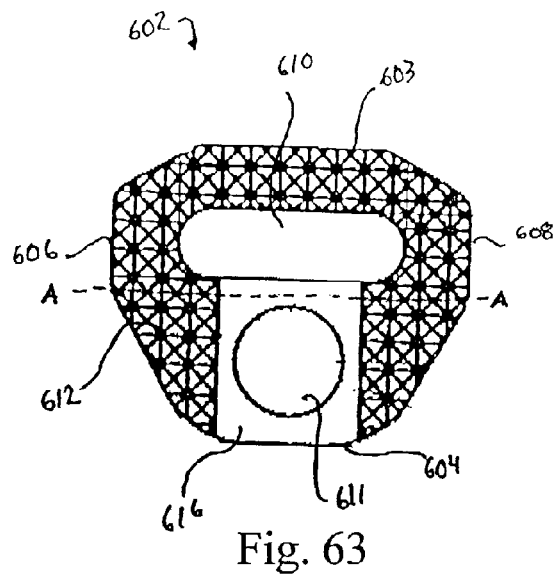
FIG. 63 is a top view of an endcap of a seventh embodiment of the present invention.
Figure 64:
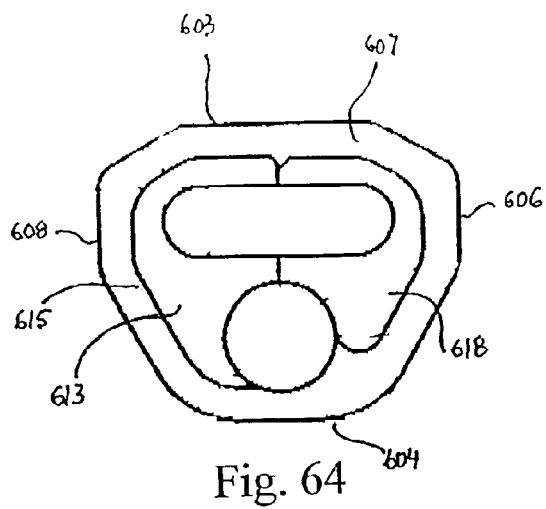
FIG. 64 is a bottom view of the endcap of FIG. 63.

In a seventh embodiment, implant 600 is similar to the previously disclosed stackable embodiment, however implant 600 has a slightly different structure and footprint. Preferably, the structure and footprint of implant 600 allows implant 600 to be particularly suited for implantation in the cervical region of the spine. FIG. 63 shows a top view of endcap 602 of implant 600. Endcap 602 has a generally oblong octagonal shaped footprint which includes anterior side 603, posterior side 604, and first and second lateral sides 606, 608.

Figure 65:
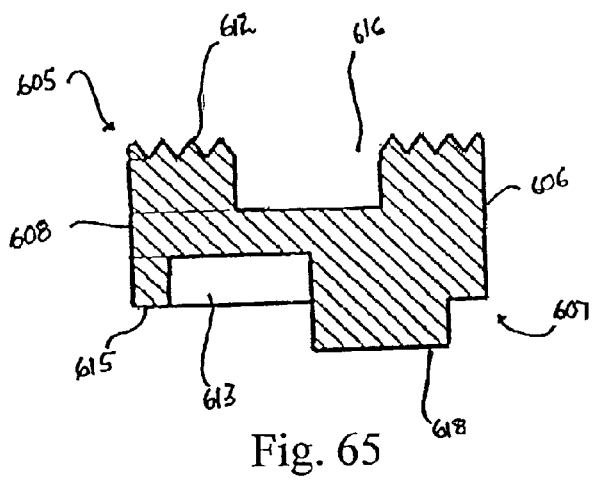
FIG. 65 is a cross-sectional view taken at line A-A of the endcap of FIG. 63.
Figure 66:
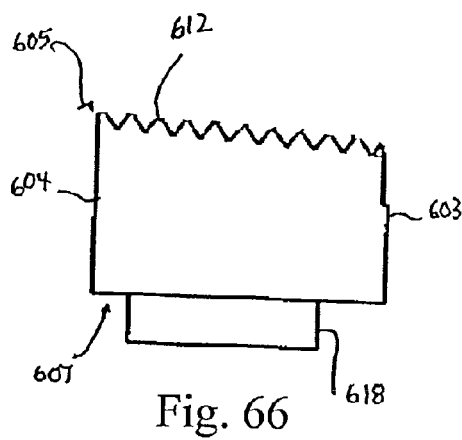
FIG. 66 is a side or lateral view of the endcap of FIG. 63.

As shown in FIGS. 63-66, endcap 602 also includes an elongated bore 610 which can be filled with bone growth inducing substances to allow bony ingrowth and to further assist in the fusion of the adjacent vertebrae. Endcap 602 further includes a central bore 611 for receiving a fastening member, such as a screw. In addition, endcap 602, on its upper surface 605, has sections or areas having gripping structures 612 to facilitate engagement of implant 600 with the end plates of the adjacent vertebra, and has sections or areas 616 which are substantially smooth and devoid of any protrusions. Although in FIG. 63 section 616 is shown as extending along a partial length of endcap 602, sections 616 may extend along the entire length of endcap 602, from perimeter edge to perimeter edge. Section 616 may be provided to provide a recess allowing a screw head to be recessed so as not to extend upwardly beyond the upper ends of the gripping structures 612. As can be seen in FIGS. 65 and 66, endcap 602 has a protrusion 618 configured and dimensioned to interface and mate with a recess portion of the implant body or another endcap. It can be appreciated that protrusion 618 may be any shape desired. A lower surface 607 surrounds the protrusion 618. Lower surface 607 is illustrated as surrounding and encircling completely protrusion 618, but it can be appreciated that lower surface 607 may only partially surround protrusion 618. Located proximate to protrusion 618, on lower surface 607, is a shoulder 615 defining a cavity 613. Cavity 613 is configured and dimensioned to interface and mate with a portion of the implant body or another endcap. Shoulder 615 has been shown as surrounding cavity 613 entirely, but it should be appreciated that shoulder 615 may only partially surround cavity 513.

Endcap 602 may have a generally wedge-shaped, side profile that is designed to restore the natural curvature or lordosis of the spine after the affected disc or affected vertebral body and adjoining discs have been removed. As shown in FIG. 66, this wedge shape results from a gradual increase in height from anterior side 603 to the posterior side 604. In an exemplary embodiment, upper surface 605 may also be a flat planar surface, a convexly-curved surface, or a substantially curved surface, preferably shaped to mimic the topography of the adjacent vertebral end plates. The radius of curvature for upper surface 605 may be the same as described for the one-piece implant described earlier.

Figure 67:
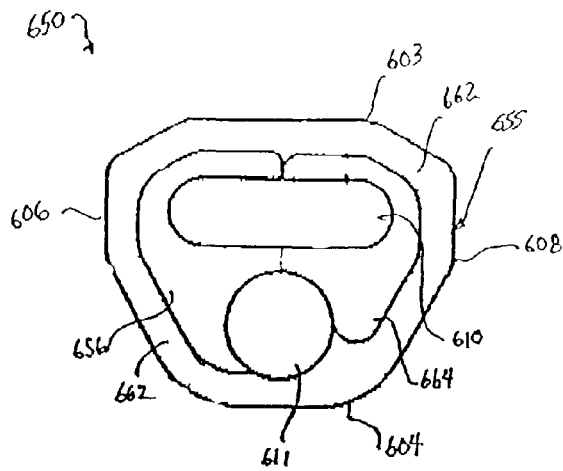
FIG. 67 is a top view of a body portion of a seventh embodiment of the present invention.
Figure 68:
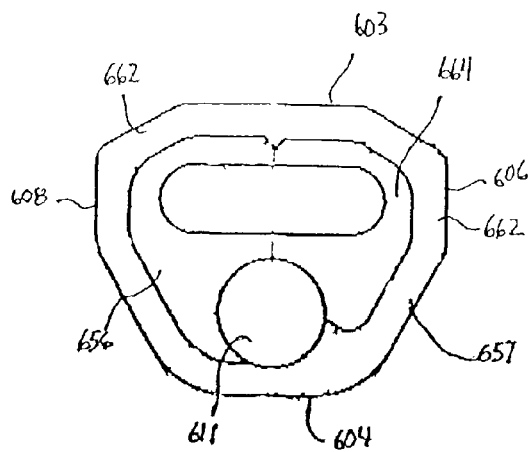
FIG. 68 is a bottom view of the body portion of FIG. 67.
Figure 69:
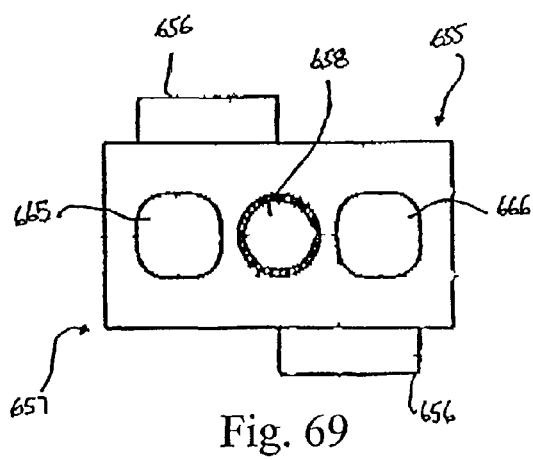
FIG. 69 is a side or lateral view of the body portion of FIG. 67.

FIG. 67 shows a top view of a body portion 650. In general, some of the structure of body portion 650 is similar or comparable to the structure of endcap 602. Accordingly, the equivalent structures of body portion 650 have been numbered the same as endcap 602 and discussion of the similar components and features is not believed necessary. As can be seen in FIGS. 67-69, body portion 650 has a generally oblong octagonal shape footprint. Located on upper surface 655 and lower surface 657, body portion 650 has a shoulder 662 defining a cavity 664 and a protrusion 656. While shoulder 662 is shown as completely enclosing and surrounding cavity 664, shoulder 662 may only partially surround cavity 664. Likewise, upper surface 655 and lower surface 657 are shown as completely surrounding protrusions 656, but it can be appreciated that upper surface 655 and lower surface 657 may only partially surround protrusions 656. Shoulder 662 and cavity 664 are configured and dimensioned to interface and mate with either protrusion 618 of endcap 602, or protrusion 656 of another body portion 650. Protrusion 656 of body portion 650 is configured and dimensioned to interface and mate with either cavity 613 of endcaps 602 or cavity 664 of another body portion 650. Again, the protrusions may be any contemplated geometric shape.

As mentioned above, implant 600 is a stackable implant comprising two endcaps 602, and, if necessary, at least one body portion 650. The modularity of implant 600, allows implant 600 to have a variable height, thereby allowing a surgeon to create an implant sized to appropriately fit the surgical space. In use, once the implant height that will be needed for the surgical procedure is determined, the desired implant can be created from the endcaps and, if necessary, one or more body portions. If a smaller implant is needed, implant 600 may comprise two endcaps 602. If a larger implant is needed, implant 600 may comprise endcaps 602, and at least one body portion 650. Body portions 650 may be the same size or of various sizes. Endcap 602, and body portion 650 are configured and dimensioned to mate with each other via an interference or similar fit. For further fixation of the endcaps or the endcaps and body portion together, a fixation screw may be threaded into central bore 611. Additional screws and bores my also be used.

Body portion 650 also may include windows 665, 666 which can be filled with bone growth inducing substances to further allow for bony ingrowth and to further assist in the fusion of the adjacent vertebrae. Windows 665, 666 may also be used to mate with the implant holder to assist with the implantation of the implant.

Body portion 650 may also have a threaded bore 658. Threaded bore 658 is sized to receive an implantation instrument such as a threaded inserter for implantation of the assembled implant 600. As can best be seen in FIG. 69, threaded bore 558 is located on lateral sides 606, 608. This location allows for insertion of implant 600 in a lateral fashion.

Figure 70:
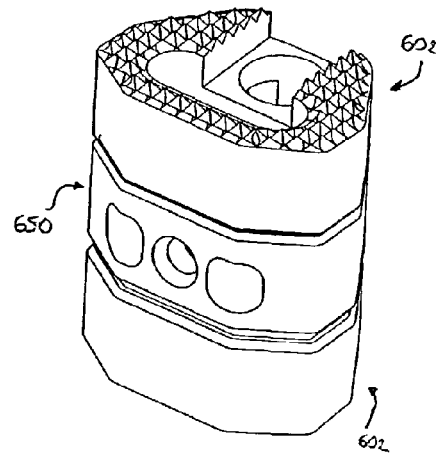
FIG. 70 is a perspective view of an implant of a seventh embodiment of the present invention.

FIG. 70 shows a perspective view of one embodiment of implant 600 which includes two endcaps 602 and one body portion 650.

The embodiments disclosed herein are illustrative and exemplary in nature and it will be appreciated that numerous modifications and other embodiments of the implant disclosed may be devised by those skilled in the art.

What is claimed:

1. A modular intervertebral implant kit for constructing an intervertebral implant comprising:
    a plurality of upper endcaps, each of the upper endcaps comprising a lower surface having at least a portion that is substantially flat, and an upper surface configured to contact a vertebral endplate, wherein at least one of the upper endcaps has a different shape or size than at least one other upper endcap and the upper surface of each upper endcap is a different shape than the lower surface of the upper endcap, and at least one of the upper endcaps comprises a convexly curved upper surface;
    a plurality of lower endcaps, each of the lower endcaps comprising an upper surface having at least a portion that is substantially flat, and a lower surface configured to contact a vertebral endplate, wherein at least one of the lower endcaps has a different shape or size than at least one other lower endcap and the lower surface of each lower endcap is a different shape than the upper surface of the lower endcap;
    a body configured to be disposed between the upper endcaps and lower endcaps, the body having a substantially flat upper surface configured to engage the substantially flat lower surface portion of the upper endcaps, and the body having a substantially flat lower surface configured to engage the substantially flat upper surface portion of the lower endcaps,
    wherein assembling at least one body between one upper endcap and one lower endcap forms an implant sized and configured for insertion between vertebral endplates.

2. The modular intervertebral implant kit of claim 1, wherein at least one of the lower endcaps has a convexly curved lower surface.

3. The modular intervertebral implant kit of claim 1, further comprising a plurality of bodies configured to be disposed between the upper endcaps and lower endcaps.

4. The modular intervertebral implant kit of claim 3, further comprising a plurality of bodies, wherein at least one of the plurality of bodies has a different shape or size than another of the plurality of bodies.

5. The modular intervertebral implant kit of claim 1, wherein the body is a different shape and configuration than either of the upper or lower endcaps.

6. The modular intervertebral implant kit of claim 1, wherein at least one of the upper and lower endcaps have at least one channel for receiving a surgical instrument.

7. The modular intervertebral implant kit of claim 6, wherein the channel runs in at least an anterior-posterior direction or a lateral direction.

8. The modular intervertebral implant kit of claim 6, wherein the at least one channel further includes at least one retaining groove for mating with a projection formed on a second surgical instrument.

9. The modular intervertebral implant kit of claim 8, wherein the at least one retaining groove is disposed near the anterior side.

10. The modular intervertebral implant kit of claim 8, wherein posterior and anterior sides of upper or lower endplates include a second channel sized and configured to receive the second surgical instrument, the second channel extending at least partially from a first lateral side to a second lateral side.

11. The modular intervertebral implant kit of claim 10, wherein the second channel extends completely from the first lateral side to the second lateral side.

12. The modular intervertebral implant kit of claim 1, wherein the upper surface of the upper endcaps and lower surface of the lower endcaps have a downward taper at an anterior end of the implant and at a posterior end of the implant to facilitate insertion of the implant.

13. The modular intervertebral implant kit of claim 1, wherein the upper and lower endcaps have a central bore configured and adapted to receive an osteoconductive material.

14. The modular intervertebral implant kit of claim 13, wherein the central bore is defined by first and second convexly curved lateral side surfaces of the implant.

15. The modular intervertebral implant kit of claim 1, wherein the upper surface of at least one of the upper endcaps has a substantially smooth area for receiving a surgical instrument.

16. The modular intervertebral implant kit of claim 15, wherein the lower surface of at least one of the lower endcaps has a substantially smooth area for receiving a surgical instrument.

17. The modular intervertebral implant kit of claim 15, wherein the upper surface of the upper endcaps include a first substantially smooth area extending from a periphery of the endcap and a second substantially smooth area extending from the periphery of the endcap, the substantially smooth areas being sized and configured to receive a surgical instrument.

18. The modular intervertebral implant kit of claim 1, wherein the lower surface of the lower endcaps include a first substantially smooth area extending from a periphery of the endcap and a second substantially smooth area extending from the periphery of the endcap, the substantially smooth areas being sized and configured to receive a surgical instrument.

19. A modular intervertebral implant kit for constructing an intervertebral implant comprising:
a plurality of upper endcaps, each of the upper endcaps comprising a lower surface having at least a portion that is substantially flat, and an upper surface configured to contact a vertebral endplate, wherein at least one of the upper endcaps has a different shape or size than at least one other upper end cap and at least one of the upper endcaps comprises a convexly curved upper surface;
a plurality of lower endcaps, each of the lower endcaps comprising an upper surface having at least a portion that is substantially flat, and a lower surface configured to contact a vertebral endplate, wherein at least one of the lower endcaps has a different shape or size than at least one other lower end cap;
a body configured for being located between the upper and lower endcaps, having a substantially flat upper surface configured to engage the substantially flat lower surface of the upper endcaps, and having a substantially flat lower surface configured to engage the substantially flat upper surface of the lower endcaps, wherein the body is a different shape than at least one of the upper and lower endcaps,
wherein assembling at least one body between one upper endcap and one lower endcap forms an implant sized and configured for insertion between intervertebral endplates.

20. The modular intervertebral implant kit of claim 19, wherein at least one of the lower endcaps has a convexly curved lower surface.

21. The modular intervertebral implant kit of claim 19, further comprising a plurality of bodies configured to be disposed between the upper endcaps and lower endcaps.

22. The modular intervertebral implant kit of claim 21, further comprising a plurality of bodies, wherein at least one of the plurality of bodies has a different shape or size than another of the plurality of bodies.

23. The modular intervertebral implant kit of claim 19, wherein the upper surface of the upper endcaps and lower surface of the lower endcaps have a downward taper at an anterior end of the implant and at a posterior end of the implant to facilitate insertion of the implant.

24. The modular intervertebral implant kit of claim 19, wherein the upper surface of at least one of the upper endcaps has a substantially smooth area for receiving a surgical instrument, wherein the substantially smooth area includes a first substantially smooth area extending from a periphery of the endcap and a second substantially smooth area extending from the periphery of the endcap, the substantially smooth areas being sized and configured to receive a surgical instrument.

25. The modular intervertebral implant kit of claim 19, wherein the lower surface of at least one of the lower endcaps has a substantially smooth area for receiving a surgical instrument, wherein the substantially smooth area includes a first substantially smooth area extending from a periphery of the endcap and a second substantially smooth area extending from the periphery of the endcap, the substantially smooth areas being sized and configured to receive a surgical instrument.

26. A modular intervertebral implant kit for constructing an intervertebral implant comprising:
a plurality of upper endcaps, each of the upper endcaps having a periphery, an upper surface configured to contact a vertebral endplate, and a lower surface having a first protrusion, a first shoulder defining a first cavity, and a relatively flat portion located around at least a portion of the periphery of the upper endcap and substantially surrounding the protrusion and cavity in the lower surface;
a plurality of lower endcaps, each of the lower endcaps having a periphery, a lower surface configured to contact a vertebral endplate, and an upper surface having a second protrusion, a second shoulder defining a second cavity, and a relatively flat portion located around at least a portion of the periphery of the second endcap and substantially surrounding the protrusion and cavity on the upper surface;
wherein the first protrusion is coupled to the second cavity, and the second protrusion is coupled to the first cavity,
at least one body configured to be disposed between the upper endcaps and lower endcaps;
wherein assembling the at least one body between one upper endcap and one lower endcap forms an implant sized and configured for insertion between intervertebral endplates.

27. The modular intervertebral implant kit of claim 26, wherein at least one of the lower endcaps has a convexly curved lower surface.

28. The modular intervertebral implant kit of claim 26, further comprising a plurality of bodies configured to be disposed between the upper endcaps and lower endcaps.

29. The modular intervertebral implant kit of claim 28, further comprising a plurality of bodies, wherein at least one of the plurality of bodies has a different shape or size than another of the plurality of bodies.

30. The modular intervertebral implant kit of claim 26, wherein the upper surface of the upper endcaps and lower surface of the lower endcaps have a downward taper at an anterior end of the implant and at a posterior end of the implant to facilitate insertion of the implant.

31. The modular intervertebral implant kit of claim 26, wherein the upper surface of at least one of the upper endcaps has a substantially smooth area for receiving a surgical instrument, wherein the substantially smooth area includes a first substantially smooth area extending from a periphery of the endcap and a second substantially smooth area extending from the periphery of the endcap, the substantially smooth areas being sized and configured to receive a surgical instrument.

32. The modular intervertebral implant kit of claim 26, wherein the lower surface of at least one of the lower endcaps has a substantially smooth area for receiving a surgical instrument, wherein the substantially smooth area includes a first substantially smooth area extending from a periphery of the endcap and a second substantially smooth area extending from the periphery of the endcap, the substantially smooth areas being sized and configured to receive a surgical instrument.

* * * * *